(12) United States Patent
Kamada et al.

(10) Patent No.: US 9,995,704 B2
(45) Date of Patent: Jun. 12, 2018

(54) GAS SENSOR ELEMENT AND GAS SENSOR

(71) Applicant: NGK SPARK PLUG CO., LTD., Nagoya-shi, Aichi (JP)

(72) Inventors: Kentaro Kamada, Komaki (JP); Masaki Nakagawa, Komaki (JP); Koji Shiotani, Kasugai (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 146 days.

(21) Appl. No.: 15/224,316

(22) Filed: Jul. 29, 2016

(65) Prior Publication Data

US 2016/0334360 A1    Nov. 17, 2016

Related U.S. Application Data

(62) Division of application No. 14/147,135, filed on Jan. 3, 2014, now Pat. No. 9,551,684.

(30) Foreign Application Priority Data

Jan. 8, 2013   (JP) .................................. 2013-000999
Feb. 26, 2013  (JP) .................................. 2013-035682
(Continued)

(51) Int. Cl.
  *G01N 27/26*   (2006.01)
  *G01N 27/00*   (2006.01)
  (Continued)

(52) U.S. Cl.
  CPC ...... *G01N 27/4071* (2013.01); *G01M 15/104* (2013.01); *G01N 27/4072* (2013.01);
  (Continued)

(58) Field of Classification Search
  CPC .......... G01N 27/26; G01N 7/00; G01N 21/00; G01N 27/00; G01N 31/00; G01N 33/00
  (Continued)

(56) References Cited

U.S. PATENT DOCUMENTS 4,810,350 A   3/1989 Mantese et al.
5,108,577 A   4/1992 Mase et al.
(Continued)

FOREIGN PATENT DOCUMENTS

JP    4165652 B2    10/2008
JP    2010-122187 A   6/2010

OTHER PUBLICATIONS

Communication dated Sep. 14, 2016 from the U.S. Patent and Trademark Office in parent U.S. Appl. No. 14/147,135.

*Primary Examiner* — Brian J. Sines
(74) *Attorney, Agent, or Firm* — Sughrue Mion, PLLC

(57) ABSTRACT

A gas sensor element which has water-permeable electrodes, and water-impermeable leads connected to the electrodes A first electrode (133) has a space exposure portion (133b) exposed to internal space (160) of a gas sensor element (10) which communicates with an ambient atmosphere. A first lead (137) is connected to the first electrode (133). The first electrode (133) includes a first connection portion (133d) which is disposed at a position not exposed to the internal space (160) and connected to the first lead (137), and which is a portion of the first electrode (133) located most distant from the internal space (160). The entire first connection portion (133d) is located in a region A1 which extends from the internal space (160) over a distance of 1.0 mm or less. Also enclosed is a gas sensor including the gas sensor element.

4 Claims, 11 Drawing Sheets

(30) Foreign Application Priority Data

Oct. 28, 2013 (JP) ................................. 2013-223457
Nov. 8, 2013 (JP) ................................. 2013-231774

(51) Int. Cl.
  *G01N 27/407* (2006.01)
  *G01M 15/10* (2006.01)
  *G01N 33/00* (2006.01)

(52) U.S. Cl.
  CPC ..... *G01N 27/4077* (2013.01); *G01N 27/4078* (2013.01); *G01N 33/0037* (2013.01)

(58) Field of Classification Search
  USPC ...... 422/83, 98, 82.01, 82.02; 204/424, 426, 204/431
  See application file for complete search history.

(56) References Cited

U.S. PATENT DOCUMENTS

| | | |
|---|---|---|
| 5,763,763 A | 6/1998 | Kato et al. |
| 5,879,525 A | 3/1999 | Kato |
| 6,344,119 B2 | 2/2002 | Kato et al. |
| 6,423,209 B1 | 7/2002 | Weber et al. |
| 7,445,700 B2 | 11/2008 | Kato et al. |
| 7,611,612 B2 | 11/2009 | Nair et al. |
| 8,921,738 B2 | 12/2014 | Heimann et al. |
| 2001/0008211 A1 | 7/2001 | Kato et al. |
| 2006/0185978 A1* | 8/2006 | Nagao ................. G01N 27/4071 204/424 |
| 2008/0067067 A1* | 3/2008 | Oya ..................... G01N 27/419 204/426 |
| 2008/0121020 A1* | 5/2008 | Oya ................... G01N 27/4071 73/31.05 |
| 2010/0155240 A1* | 6/2010 | Matsuoka .......... G01N 27/4077 204/424 |
| 2011/0036716 A1* | 2/2011 | Sekiya ............... G01N 27/4077 204/424 |
| 2011/0209523 A1* | 9/2011 | Otsubo .............. G01N 27/4077 73/23.31 |
| 2012/0018305 A1* | 1/2012 | Yoshikawa ........ G01N 27/4077 204/431 |
| 2012/0055234 A1* | 3/2012 | Yonezu .............. G01N 27/4077 73/31.05 |
| 2012/0160012 A1* | 6/2012 | Kato .................... G01N 27/419 73/31.05 |

* cited by examiner

GAS SENSOR ELEMENT AND GAS SENSOR

CROSS-REFERENCE TO RELATED APPLICATIONS

This is a Rule 53(b) Divisional Application of U.S. application Ser. No. 14/147,135 filed Jan. 3, 2014, which claims benefit of Japanese Patent Application No. 2013-000999 filed on Jan. 8, 2013, Japanese Patent Application No. 2013-035682 filed on Feb. 26, 2013; Japanese Patent Application No. 2013-223457 filed on Oct. 28, 2013 and Japanese Patent Application No. 2013-231774 filed Nov. 8, 2013, the contents of all of which are incorporated herein by reference in their entirety.

BACKGROUND OF THE INVENTION

1. Field of the Invention

The present invention relates to a gas sensor element, and to a gas sensor including the gas sensor element.

2. Description of the Related Art

A conventionally known gas sensor is attached to an exhaust path of an internal combustion engine such as an automotive engine for detecting a concentration of oxygen or a concentration of $NO_x$ in exhaust gas (gas to be measured) (refer to Patent Documents 1 and 2). Patent Documents 1 and 2 describe a gas sensor element used in the gas sensor and configured such that a plurality of platelike solid electrolyte bodies are laminated together. The gas sensor element includes electrodes provided on the front sides or back sides of the solid electrolyte bodies, and leads provided on the front sides or back sides of the solid electrolyte bodies and connected to the electrodes.

In Patent Documents 1 and 2, in order to ensure oxygen pumping performance, the electrodes are porous; as a result, the electrodes have gas permeability and water permeability. In contrast, the leads are formed to be dense since, in order to improve electrical conductivity, high density per unit area is desired. As a result, the leads are gas-impermeable and water-impermeable.

[Patent Document 1] Japanese Patent No. 4165652
[Patent Document 2] Japanese Patent Application Laid-Open (kokai) No. 2010-122187

3. Problems to be Solved by the Invention

FIGS. 3 and 4 in Patent Document 1 show a first electrode having a space exposure portion which is exposed to an internal space communicating with an ambient atmosphere of the gas sensor element. Furthermore, FIGS. 3 and 4 show a first lead connected to the first electrode. The first lead is connected to the first electrode within the internal space so as to overlap the first electrode. However, in the case of combining the water-permeable first electrode and the water-impermeable first lead as mentioned above, the following problem may arise. That portion (hereinafter, referred to as a first connection portion) of the first electrode which overlaps the first lead may deteriorate in oxygen pumping performance, with a resultant deterioration in accuracy in detecting a concentration of oxygen or a concentration of $NO_x$ in a gas to be measured.

In view of the above problem, there is a proposal to extend a portion of the electrode to a position which is not exposed to the internal space, in order to dispose the first connection portion at a position not exposed to the internal space. This can restrain deterioration in accuracy in detecting a concentration of oxygen or a concentration of $NO_x$ in gas to be measured, as a result of deterioration in oxygen pumping performance stemming from disposition of the first connection portion within the internal space.

However, even though the first connection portion is disposed at a position not exposed to the internal space, the following problem may arise. For example, in winter, water may condense on the surface of the gas sensor element. Water formed through condensation (condensed water) may penetrate into the internal space of the gas sensor element and further into the water-permeable first electrode through the space exposure portion. Water which has penetrated into the first electrode reaches the first connection portion connected to the first lead. Since the first lead is water-impermeable, water fails to penetrate into the first lead; as a result, water may stagnate in the first connection portion. When condensed water stagnating in the first connection portion freezes and thus expands in volume, stress is generated in such a direction as to separate layers between which the first connection portion is sandwiched, potentially generating a crack between the layers.

The present invention has been made to solve the above problems, and an object thereof is to provide a gas sensor element which has water-permeable electrodes, and water-impermeable leads connected to the electrodes and which, even when water penetrates into the water-permeable electrodes, can prevent generation of cracks therein without deterioration in oxygen pumping performance of the electrodes, as well as a gas sensor including the gas sensor element.

SUMMARY OF THE INVENTION

The above object has been achieved, in accordance with a first aspect (1) of the present invention, by providing a gas sensor element configured as a laminate of platelike solid electrolyte bodies. The gas sensor element comprises electrodes provided on front sides or back sides of the solid electrolyte bodies, and leads provided on the front sides or the back sides of the solid electrolyte bodies and connected to the electrodes, respectively. The electrodes include a water-permeable first electrode having a space exposure portion exposed to an internal space of the gas sensor element which communicates with an ambient atmosphere of the gas sensor element. The leads include a water-impermeable first lead connected to the first electrode. The first electrode includes a first connection portion which is disposed at a position not exposed to the internal space and connected to the first lead, and which is a portion of the first electrode located most distant from the internal space. The entire first connection portion is located in a region which extends from the internal space over a distance of 1.0 mm or less.

The gas sensor element has a water-permeable first electrode exposed to an internal space of the gas sensor element which communicates with the ambient atmosphere of the gas sensor element, and a water-impermeable first lead connected to the first electrode. The first electrode includes a first connection portion disposed at a position not exposed to the internal space, and connected to the first lead (thus, the first electrode has a space exposure portion exposed to the internal space, and the first connection portion that is not exposed to the internal space). For connection to the first lead at a position located externally of the internal space, the first connection portion is formed as an extension of the first electrode; thus, the first connection portion is a portion of the first electrode located most distant from the internal space.

Conventionally, a thus-configured gas sensor element has involved a risk of generation of cracks therein as a result of freezing of water which has penetrated into the first connection portion. Specifically, for example, water condensed on the surface of the gas sensor element may penetrate into the internal space of the gas sensor element and further into the first electrode through the space exposure portion. Water which has penetrated into the first electrode reaches the first connection portion connected to the first lead and may stagnate in the first connection portion, since the first lead is water-impermeable. When condensed water stagnating in the first connection portion freezes and thus expands in volume, stress is generated in such a direction as to separate layers between which the first connection portion is sandwiched, potentially generating a crack between the layers (between which the first connection portion is sandwiched) of the gas sensor element.

By contrast, in the above-mentioned gas sensor element, the entire first connection portion is disposed in a region which extends from the internal space over a distance of 1.0 mm or less. Thus, even when water penetrates into the first connection portion and then freezes, generation of cracks in the gas sensor element can be prevented. A conceivable reason for this is as follows.

As water stagnating in the first connection portion begins to freeze, pores in the first connection portion gradually reduce in volume (ice gradually closes pores); thus, water stagnating in the first connection portion moves in a direction opposite the first lead (i.e., toward the internal space having sufficient space for allowing penetration of water). At this time, since the entire first connection portion is disposed in the region which extends from the internal space over a distance of 1.0 mm or less (i.e., a short distance of 1.0 mm or less is provided between the internal space and that portion of the first connection portion which is most distant from the internal space), most of water stagnating in the first connection portion can be moved (released) to the internal space before freezing in the first connection portion. Subsequently, even though most water freezes and thus expands within the internal space, no stress is generated in such a direction as to separate the layers of the gas sensor element. As a result, generation of cracks in the gas sensor element can be prevented.

Notably, "the internal space of the gas sensor element which communicates with an ambient atmosphere of the gas sensor element" encompasses an internal space which directly (with no interposition existing) communicates with the ambient atmosphere of the gas sensor, and an internal space which communicates with the ambient atmosphere through a porous body (an internal space which communicates in a gas-permeable and water-permeable manner). The internal space which communicates with the ambient atmosphere through a porous body is not limited to an internal space which communicates with the ambient atmosphere through a single porous body, but encompasses an internal space which communicates with the ambient atmosphere through a plurality of porous bodies (i.e., which communicates in a gas-permeable and water-permeable manner).

Additionally, in the above-mentioned gas sensor element, the first electrode is connected to the first lead at a position not exposed to the internal space. Thus, in contrast to Patent Document 1 (Japanese Patent No. 4165652) mentioned above, "deterioration in accuracy in detecting a concentration of oxygen or a concentration of $NO_x$ in gas to be measured, as a result of deterioration in oxygen pumping performance stemming from disposition of the first connection portion within the internal space" can be restrained.

In a preferred embodiment (2), the above gas sensor element (1) further comprises a first insulation layer formed on the front side or the back side of the solid electrolyte body and is configured as follows: the first lead and a portion of the first electrode are formed on the first insulation layer; the space exposure portion of the first electrode has an electrolyte body contact portion which is in contact with the solid electrolyte body through a through hole extending through the first insulation layer in a laminating direction of the solid electrolyte body; and the first connection portion of the first electrode is connected to the first lead on the first insulation layer.

In the above-mentioned gas sensor element, the space exposure portion (a portion exposed to the internal space of the gas sensor element) of the first electrode has an electrolyte body contact portion which is in contact with the solid electrolyte body through a through hole extending through the first insulation layer. Meanwhile, the first lead is formed on the first insulation layer (and is thus not in contact with the solid electrolyte body). Also, the first connection portion of the first electrode is connected to the first lead on the first insulation layer. Therefore, in the above-mentioned gas sensor element, the first connection portion of the first electrode is disposed at a position not exposed to the internal space and is not in contact with the solid electrolyte body.

Thus, in the above-mentioned gas sensor, only the electrolyte body contact portion of the first electrode can actually function as a sensing portion, and an object of detection; i.e., gas concentration, can be accurately detected. The lead differs from the first electrode in electrical characteristics; therefore, in a configuration in which the lead and the first connection portion connected to the lead are partially in contact with solid electrolyte, gas concentration may fail to be accurately detected.

In another preferred embodiment (3), either one of the above sensor elements (1) or (2) is configured as follows: the electrodes include a water-permeable second electrode having a porous body contact portion in contact with a porous body having gas permeability and water permeability and exposed to the ambient atmosphere of the gas sensor element; the leads include a water-impermeable second lead connected to the second electrode; the second electrode includes a second connection portion which is connected to the second lead at a position located away from the porous body with respect to a planar direction orthogonal to the laminating direction of the solid electrolyte body and which is a portion of the second electrode disposed most distant from the porous body; and the entire second connection portion is located in a region which extends from the porous body over a distance of 1.0 mm or less.

The above-mentioned gas sensor element has a porous body having gas permeability and water permeability and exposed to the ambient atmosphere of the gas sensor element. Furthermore, the above-mentioned gas sensor element has a water-permeable second electrode having a porous body contact portion in contact with the porous body, and the water-impermeable second lead connected to the second electrode. The second electrode has a second connection portion connected to the second lead at a position located away from the porous body with respect to a planar direction (therefore, the second electrode has a porous body contact portion in contact with the porous body, and the second connection portion not in contact with the porous body). For connection to the second lead at a position located away from the porous body, the second connection portion is formed through extension of the second electrode; therefore, the second connection portion is a portion of the second electrode located most distant from the porous body.

Conventionally, even a gas sensor element having such a configuration involves a risk of generation of cracks therein as a result of freezing of water which has penetrated into the second connection portion. Specifically, for example, water condensed on the surface of the gas sensor element may penetrate into the second electrode through the porous body in contact with the second electrode. Water which has penetrated into the second electrode reaches the second connection portion connected to the second lead and may stagnate in the second connection portion, since the second lead is water-impermeable. When condensed water stagnating in the second connection portion freezes and thus expands in volume, stress is generated in such a direction as to separate layers between which the second connection portion is sandwiched, potentially generating a crack between the layers (between which the second connection portion is sandwiched) of the gas sensor element.

By contrast, in the above-mentioned gas sensor element, the entire second connection portion is disposed in a region which extends from the porous body over a distance of 1.0 mm or less. Thus, even when water penetrates into the second connection portion and then freezes, generation of cracks in the gas sensor element can be prevented. A conceivable reason for this is as follows.

As water stagnating in the second connection portion begins to freeze, pores in the second connection portion gradually reduce in volume (ice gradually closes pores); thus, water stagnating in the second connection portion moves in a direction opposite the second lead (i.e., toward the porous body having sufficient space for allowing penetration of water). At this time, since the entire second connection portion is disposed in the region which extends from the porous body over a distance of 1.0 mm or less (i.e., a short distance of 1.0 mm or less is provided between the porous body and that portion of the second connection portion which is most distant from the porous body), most of the water stagnating in the second connection portion can be moved (released) to the porous body before freezing in the second connection portion. Subsequently, even though most water freezes and thus expands within the porous body, no stress is generated in such a direction as to separate the layers of the gas sensor element. Since the porous body is exposed to the ambient atmosphere, even when the porous body is filled with water, in the course of freezing, water can be released to the ambient atmosphere; therefore, no stress is generated in such a direction as to separate the layers of the gas sensor element. As a result, generation of cracks in the gas sensor element can be prevented.

Additionally, the second electrode is connected to the second lead at a position located away from the porous body with respect to a planar direction. Thus, "deterioration in accuracy in detecting a concentration of oxygen or a concentration of $NO_x$ in gas to be measured, as a result of deterioration in oxygen pumping performance stemming from disposition of the second connection portion at such a position as to overlap the porous body" can be restrained.

In yet another preferred embodiment (4), the above gas sensor element (3) has a second insulation layer formed on the front side or the back side of the solid electrolyte body; the second lead and a portion of the second electrode are formed on the second insulation layer; the porous body contact portion of the second electrode has an electrolyte body contact portion which is in contact with the solid electrolyte body through a through hole extending through the second insulation layer in the laminating direction; and the second connection portion of the second electrode is connected to the second lead on the second insulation layer.

In the above gas sensor element, the porous body contact portion (a portion in contact with the porous portion) of the second electrode has an electrolyte body contact portion which is in contact with the solid electrolyte body through a through hole extending through the second insulation layer. Meanwhile, the second lead is formed on the second insulation layer (and is thus not in contact with the solid electrolyte body). Also, the second connection portion of the second electrode is connected to the second lead on the second insulation layer. Therefore, in the above-mentioned gas sensor element, the second connection portion of the second electrode is disposed at a position located away from the porous body in a planar direction and is not in contact with the solid electrolyte body.

Thus, in the above-mentioned gas sensor, only the electrolyte body contact portion of the second electrode can actually function as a sensing portion; thus, an object of detection; i.e., gas concentration, can be accurately detected. The lead differs from the second electrode in electrical characteristics; therefore, in a configuration in which the lead and the second connection portion connected to the lead are partially in contact with solid electrolyte, gas concentration may fail to be accurately detected.

In a second aspect (5), the present invention provides a gas sensor element configured as a laminate of platelike solid electrolyte bodies. The gas sensor element comprises electrodes provided on front sides or back sides of the solid electrolyte bodies, and leads provided on the front sides or the back sides of the solid electrolyte bodies and connected to the electrodes, respectively. The electrodes include a water-permeable third electrode disposed within that internal space of the gas sensor element which communicates with an ambient atmosphere of the gas sensor element. The leads include a water-impermeable third lead connected to the third electrode. The gas sensor element has a third insulation layer formed on the front side or the back side of the solid electrolyte body. The third lead and a portion of the third electrode are formed on the third insulation layer. The third electrode has an electrolyte body contact portion which is in contact with the solid electrolyte body through a through hole extending through the third insulation layer in a laminating direction of the solid electrolyte body, and a third connection portion connected to the third lead on the third insulation layer within the internal space.

The above-mentioned gas sensor element has a water-permeable third electrode disposed within an internal space of the gas sensor element which communicates with the ambient atmosphere of the gas sensor element. That is, the entire third electrode is disposed within the internal space (the entire front or back surface of the third electrode is exposed to the internal space). Also, the gas sensor element has a water-impermeable third lead which is connected to the third connection portion within the internal space.

By employing such a configuration, even when water which has penetrated into the third electrode freezes, generation of cracks in the gas sensor element can be prevented, for the following reason. Since the entirety of the third electrode including the third connection portion is disposed within the internal space, water which stagnates in the third electrode including the third connection portion is allowed to freeze (expand) within the internal space; as a result, generation of stress in such a direction as to separate the layers of the gas sensor element can be restrained.

Additionally, the third connection portion of the third electrode is connected to the third lead on the third insulation layer (and is thus not in contact with the solid electrolyte body). Therefore, although the third connection portion is disposed within the internal space, the third connection portion does not affect oxygen pumping performance of the third electrode (the third connection portion does not deteriorate oxygen pumping performance of the third electrode). Thus, deterioration in accuracy in detecting a concentration of oxygen or a concentration of $NO_x$ in a gas to be measured can be restrained.

In a preferred embodiment (6), the above gas sensor element is configured as follows: the electrodes include a water-permeable fourth electrode which is in contact with a porous body having gas permeability and water permeability and exposed to an ambient atmosphere of the gas sensor element and which is disposed at such a position that the entirety thereof faces the porous body with respect to the laminating direction of the solid electrolyte body; the leads include a water-impermeable fourth lead connected to the fourth electrode; the gas sensor element has a fourth insulation layer formed on the front side or the back side of the solid electrolyte body; the fourth lead and a portion of the fourth electrode are formed on the fourth insulation layer; and the fourth electrode has an electrolyte body contact portion which is in contact with the solid electrolyte body through a through hole extending through the fourth insulation layer in the laminating direction and a fourth connection portion connected to the fourth lead on the fourth insulation layer at such a position as to face the porous body with respect to the laminating direction.

The above-mentioned gas sensor element has a porous body having gas permeability and water permeability and exposed to the ambient atmosphere of the gas sensor element. Furthermore, the above-mentioned gas sensor element has a water-permeable fourth electrode which is in contact with the porous body and is disposed at such a position that the entirety thereof faces the porous body with respect to the laminating direction of the solid electrolyte body (thickness direction). "The entirety of the fourth electrode faces the porous body" encompasses a case where the entirety of the fourth electrode is in contact with and faces the porous body, as well as a case where the entirety of the fourth electrode faces the porous body such that while a portion of the fourth electrode faces the porous body with the lead sandwiched therebetween, the remaining portion of the fourth electrode is in contact with and thus faces the porous body. Also, the above-mentioned gas sensor element has a fourth lead connected to the fourth connection portion of the fourth electrode at such a position as to face the porous body with respect to the laminating direction.

By employing such a configuration, even when water which has penetrated into the fourth electrode freezes, generation of cracks in the gas sensor element can be prevented, for the following reason. Since the entirety of the fourth electrode including the fourth connection portion is disposed in such a manner as to face the porous body, and the entire fourth electrode or most of the fourth electrode remaining after removing a portion in contact with the lead is in contact with the porous body, most of water stagnating in the fourth electrode is allowed to freeze (expand) within pores of the porous body; as a result, generation of stress in such a direction as to separate the layers of the gas sensor element can be restrained.

Additionally, the fourth connection portion of the fourth electrode is connected to the fourth lead on the fourth insulation layer (and is thus not in contact with the solid electrolyte body). Therefore, although the fourth connection portion is disposed at such a position as to overlap the porous body (at such a position as to face the porous body with respect to the laminating direction), the fourth connection portion does not affect oxygen pumping performance of the fourth electrode (the fourth connection portion does not deteriorate oxygen pumping performance of the fourth electrode). Thus, deterioration in accuracy in detecting a concentration of oxygen or a concentration of $NO_x$ in a gas to be measured can be restrained.

In yet another preferred embodiment (7) of any one of the above gas sensor elements (1)-(6), the gas sensor element detects a concentration of $NO_x$ contained in a gas to be measured, and an electric current flows through the first lead or the third lead according to $NO_x$ concentration.

In order to accurately detect a concentration of $NO_x$ contained in a gas to be measured (e.g., exhaust gas from an internal combustion engine), a lead through which electric current flows according to $NO_x$ concentration must be formed so as to be dense. The densely formed lead becomes water-impermeable. Thus, conventionally, in the case where an electrode is connected to a lead through which an electric current flows according to $NO_x$ concentration, when, as mentioned above, water penetrates into the electrode and then freezes, the gas sensor element involves the risk of generation of cracks therein.

However, the above-mentioned gas sensor element has, as the first or third lead, a lead through which an electric current flows according to $NO_x$ concentration. As mentioned above, the entire first connection portion of the first electrode connected to the first lead is disposed in a region which extends from the internal space over a distance of 1.0 mm or less. The third connection portion of the third electrode connected to the third lead is disposed within the internal space. Thus, even when water penetrates into the first (third) electrode and then freezes, generation of cracks in the gas sensor element can be prevented.

In yet another preferred embodiment (8), the present invention provides a gas sensor comprising any one of the above-mentioned gas sensor elements (1)-(7).

This gas sensor has any one of the above-mentioned gas sensor elements. Thus, in this gas sensor, even when water penetrates into a water-permeable electrode and then freezes, generation of cracks in the gas sensor element can be prevented without deterioration in oxygen pumping performance of the electrode; thus, the gas to be measured can be appropriately detected.

DESCRIPTION OF REFERENCE NUMERALS

Figure 1:
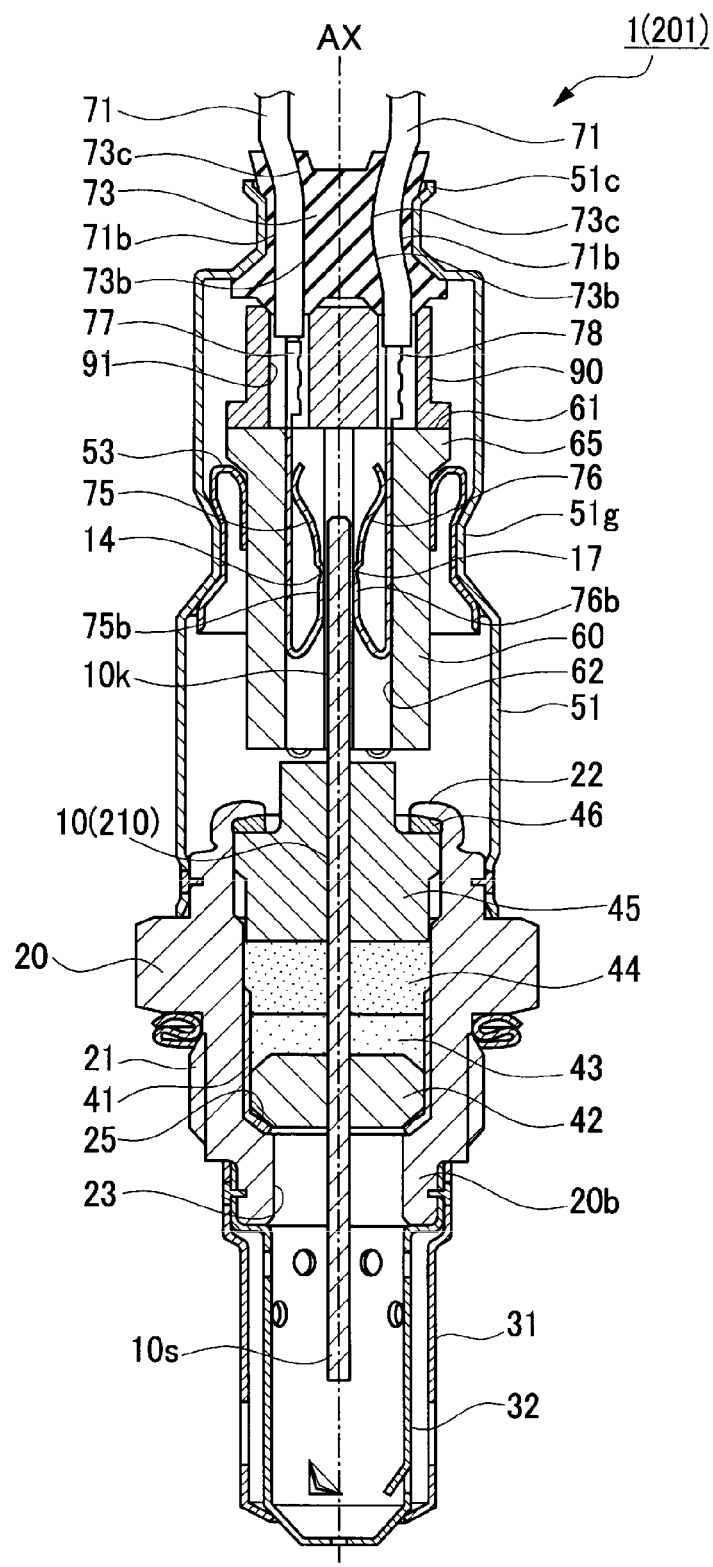
FIG. 1 is a sectional view of a gas sensor according to an embodiment and a modified embodiment of the present invention.

Reference numerals used to identify various structural features in the drawings including the following:
1, 201: gas sensor
10, 210: gas sensor element
111, 121, 131: solid electrolyte body
111b, 121b, 131b: front surface of solid electrolyte body
111c, 121c, 131c: back surface of solid electrolyte body
112: Ip1 positive electrode (second electrode)
112b: porous body contact portion
112c: electrolyte body contact portion
112d: connection portion (second connection portion)
113: Ip1 negative electrode (first electrode)
113b, 122b, 133b: space exposure portion
113c, 122c, 133c: electrolyte body contact portion
113d, 122d, 133d: connection portion (first connection portion)
114: first porous body
116: Ip1 positive lead (second lead)
117: Ip1 negative lead (first lead)
118: alumina insulation layer (second insulation layer)
118b, 119b, 128b, 138c: through hole
119, 128, 138: alumina insulation layer (first insulation layer)
122: Vs negative electrode (first electrode)
123: Vs positive electrode
126: Vs negative lead (first lead)
127: Vs positive lead
132: Ip2 positive electrode
133: Ip2 negative electrode (first electrode)
136: Ip2 positive lead
137: Ip2 negative lead (first lead)
150: first measuring chamber (internal space)
151: second porous body
160: second measuring chamber (internal space)
212: Ip1 positive electrode (fourth electrode)
212c: electrolyte body contact portion (fourth electrolyte body contact portion)
212d: connection portion (fourth connection portion)
216: Ip1 positive lead (fourth lead)
218: alumina insulation layer (fourth insulation layer)
233: Ip2 negative electrode (third electrode)
233c: electrolyte body contact portion (third electrolyte body contact portion)
233d: connection portion (third connection portion)
237: Ip2 negative lead (third lead)
238: alumina insulation layer (third insulation layer)

DETAILED DESCRIPTION OF THE PREFERRED EMBODIMENTS

Embodiment

An embodiment of the present invention will next be described with reference to the drawings. However, the present invention should not be construed as being limited thereto.

Figure 2:
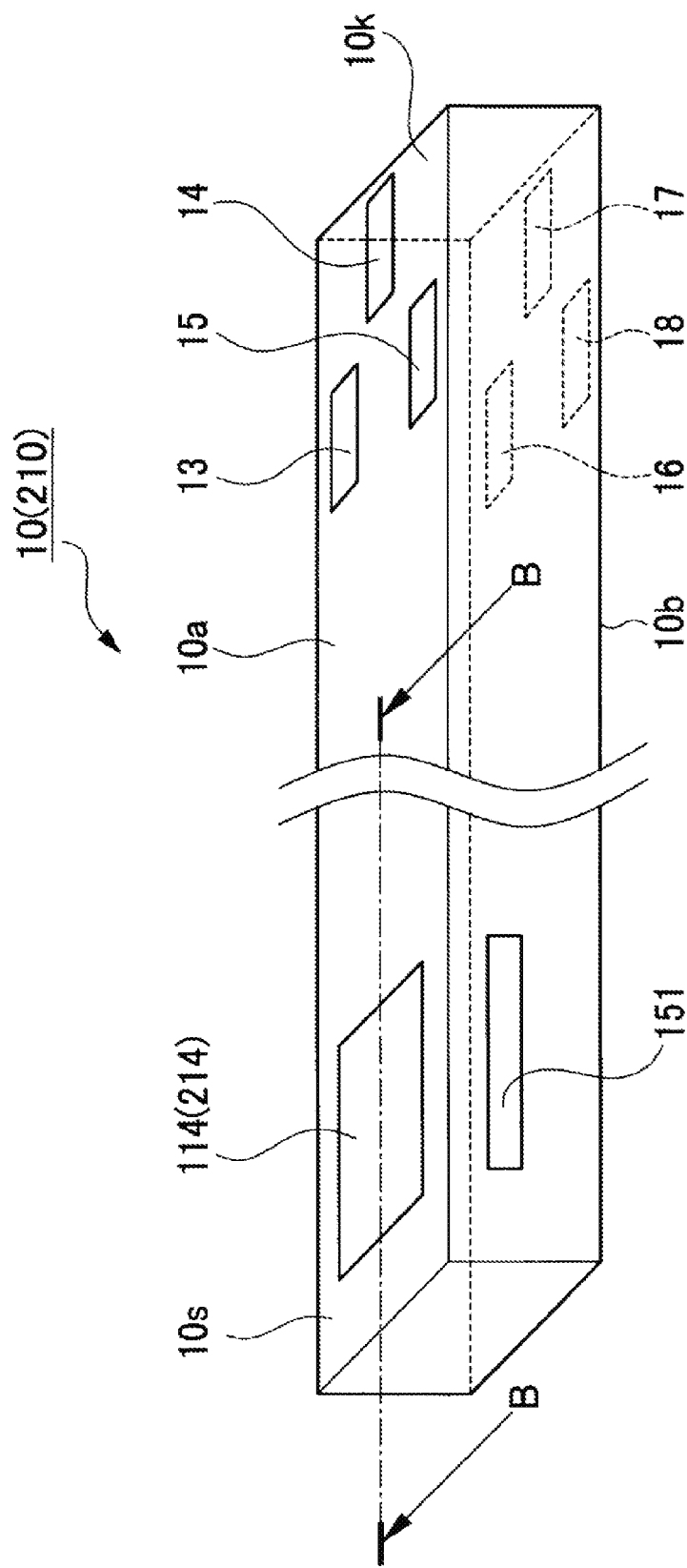
FIG. 2 is a perspective view of a gas sensor element according to the embodiment and the modified embodiment.
Figure 3:
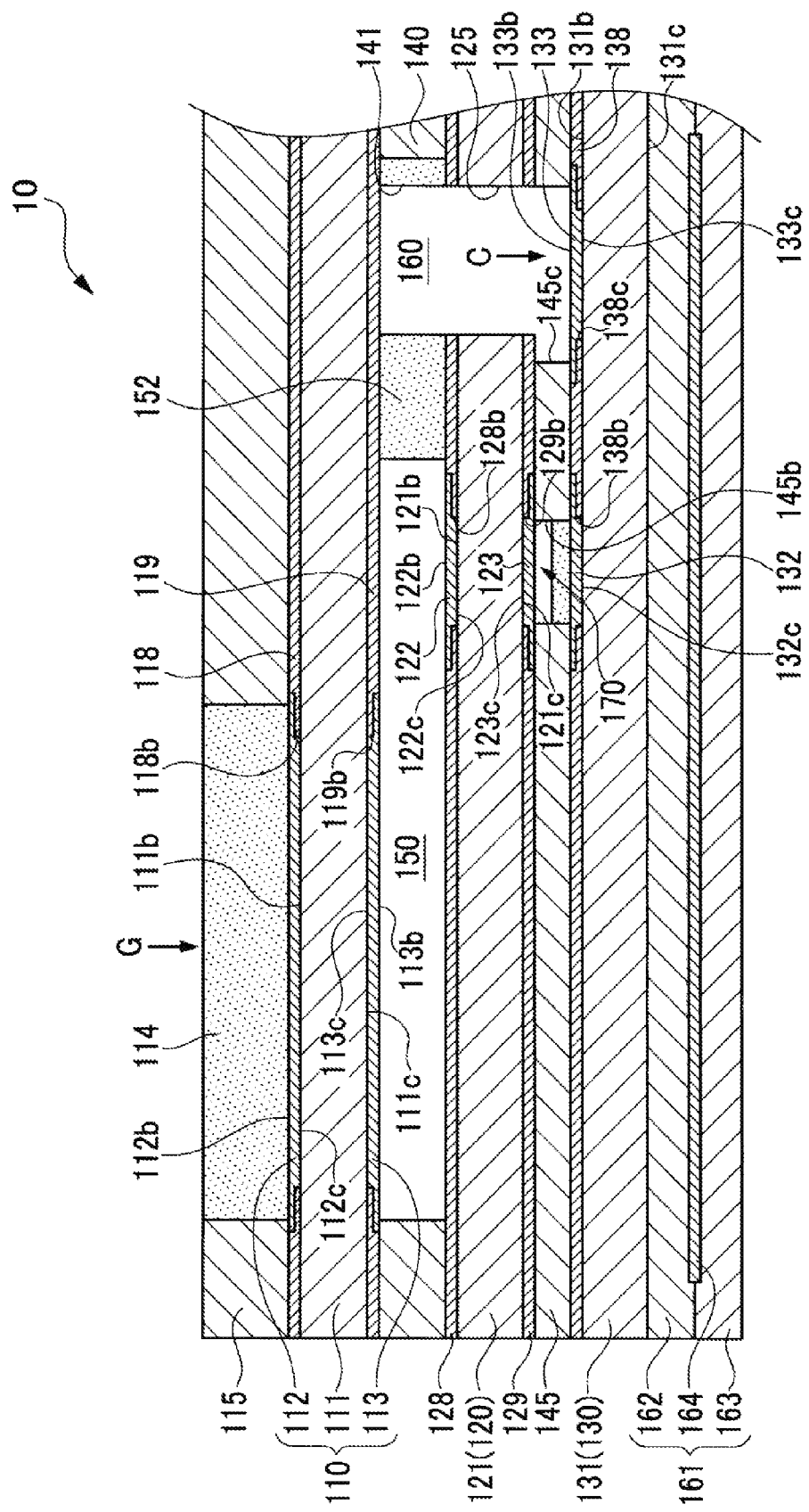
FIG. 3 is a sectional view taken along line B-B of FIG. 2.
Figure 4:
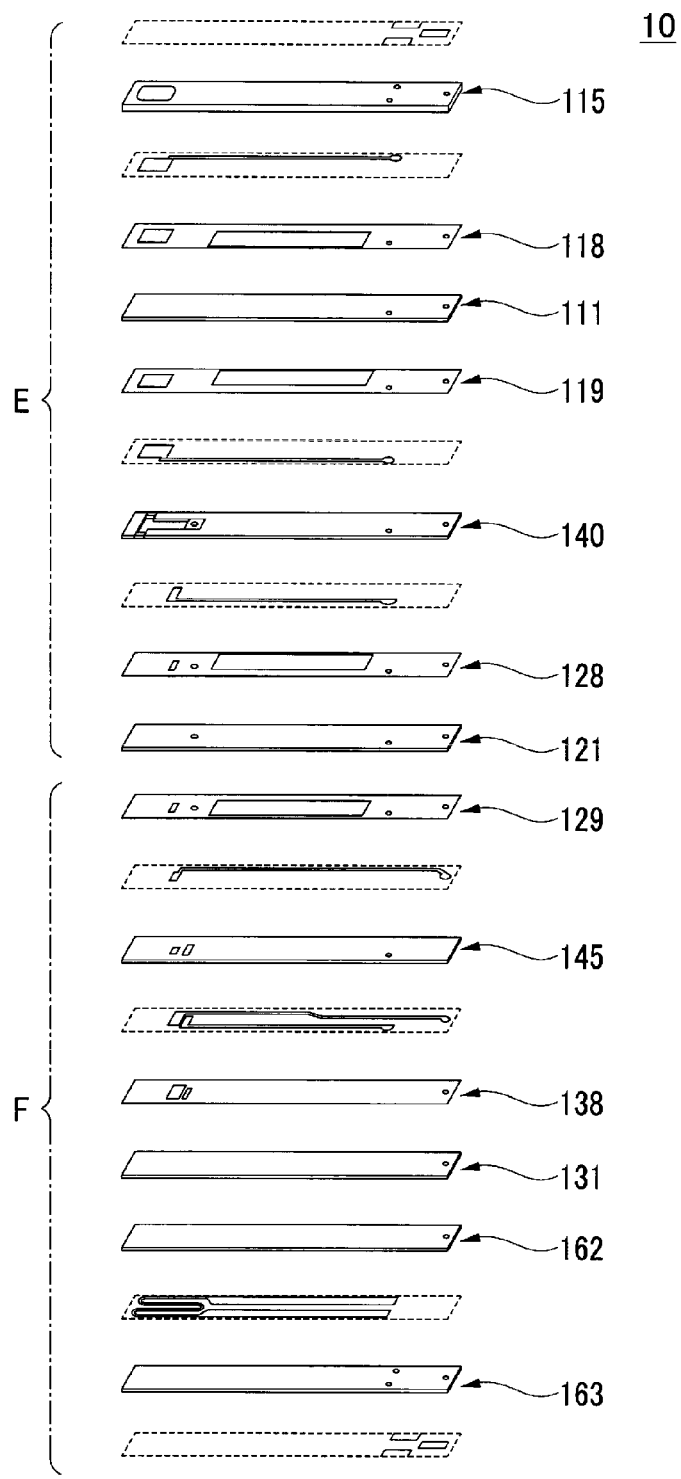
FIG. 4 is a perspective view showing component layers of the gas sensor element.
Figure 5:
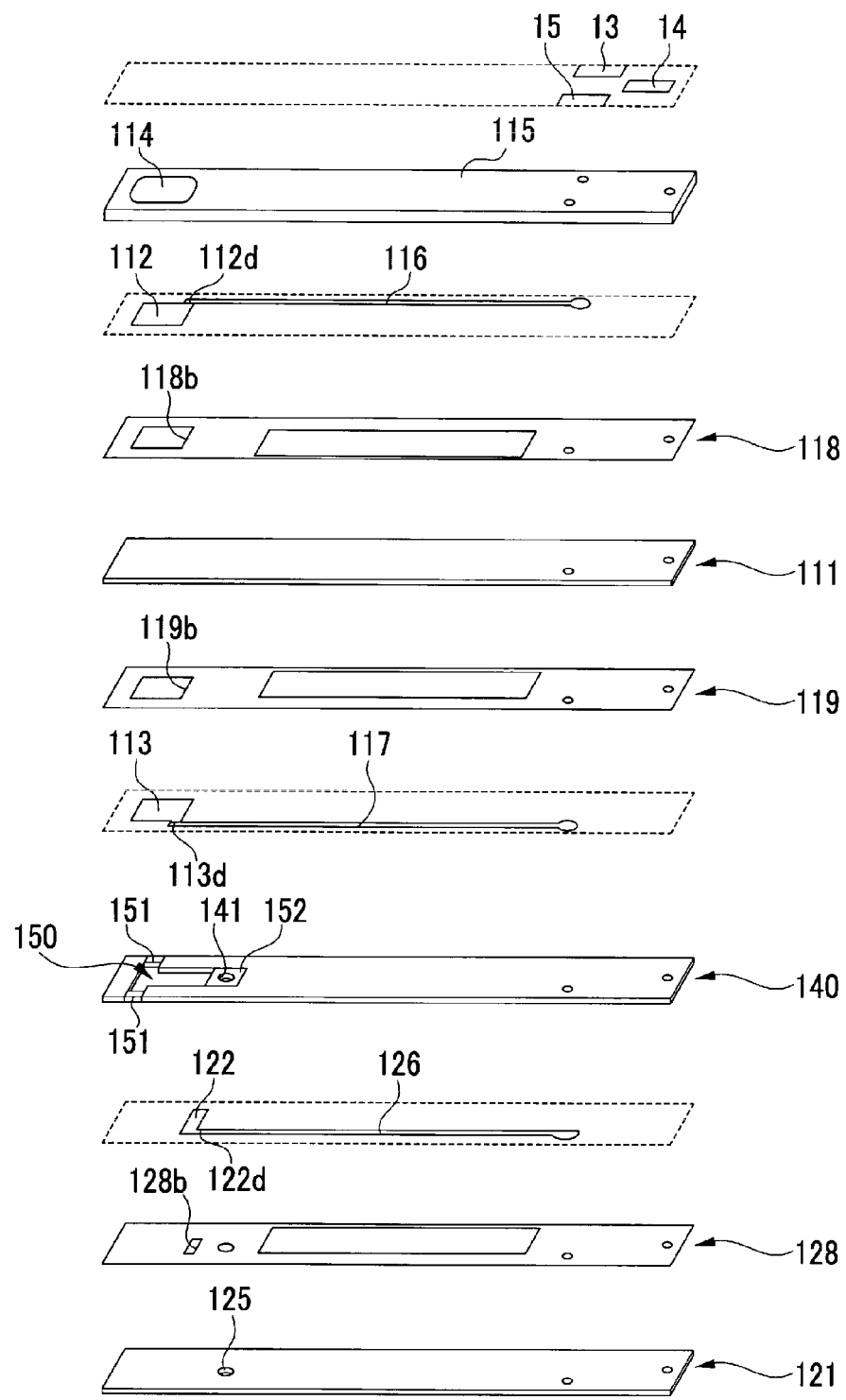
FIG. 5 is an enlarged view of region E of FIG. 4.
Figure 6:
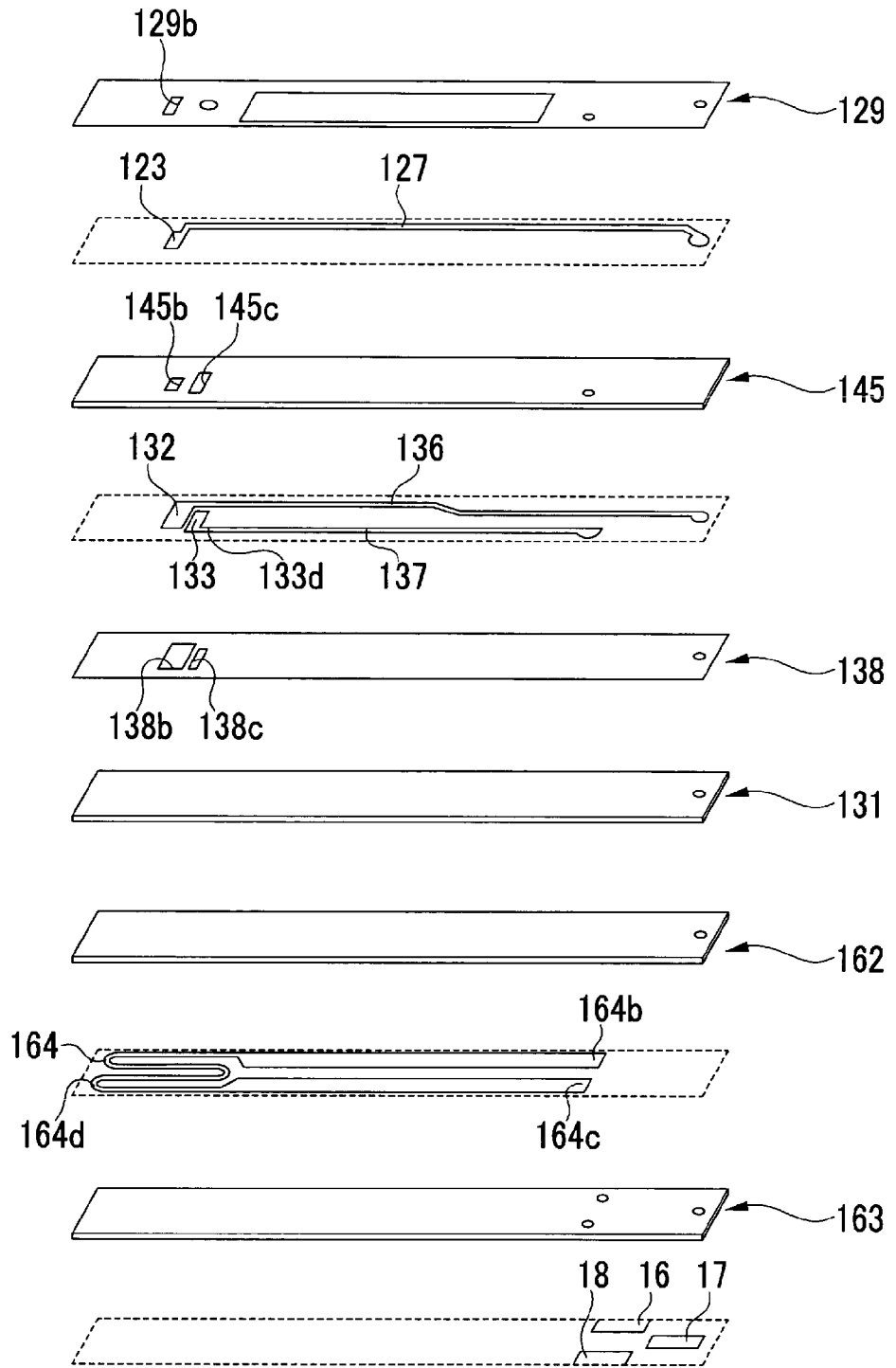
FIG. 6 is an enlarged view of region F of FIG. 4.

FIG. 1 is a longitudinal sectional view (sectional view cut along an axial line AX) of a gas sensor 1 according to the present embodiment. FIG. 2 is a perspective view of a gas sensor element 10 according to the present embodiment. FIG. 3 is a sectional view taken along line B-B of FIG. 2, showing an internal structure of the gas sensor element 10. FIG. 4 is a perspective view showing component layers of the gas sensor element 10 in the order of lamination along the laminating direction (along the vertical direction in FIG. 4). FIG. 5 is an enlarged view of region E of FIG. 4, and FIG. 6 is an enlarged view of region F of FIG. 4.

The gas sensor 1 is a $NO_x$ sensor having the gas sensor element 10 capable of detecting a concentration of a particular gas ($NO_x$) contained in exhaust gas, which is a gas to be measured, and attached, for use, to an exhaust pipe (not shown) of an internal combustion engine (see FIG. 1). The gas sensor 1 includes a tubular metallic shell 20 having a threaded portion 21 formed on its outer surface at a predetermined position for fixing the gas sensor 1 to the exhaust pipe. The gas sensor element 10 has a narrow, elongated plate shape extending in the direction of the axial line AX and is held in the interior of the metallic shell 20 (see FIGS. 1 and 2).

More specifically, the gas sensor 1 includes a holding member 60 having an insertion hole 62 into which a rear end portion 10k (an upper end portion in FIG. 1) of the gas sensor element 10 is inserted, and six terminal members held in the interior of the holding member 60. FIG. 1 shows only two terminal members (specifically, terminal members 75 and 76) out of six terminal members.

A total of six electrode terminals, each having a rectangular shape as viewed in plane, are formed on the rear end portion 10k (a right end portion in FIG. 2) of the gas sensor element 10. Specifically, electrode terminals 13, 14 and 15 are formed on a first surface 10a of the gas sensor element 10, and electrode terminals 16, 17 and 18 are formed on a second surface 10b. The terminal members are in elastic contact with and thus are electrically connected to the electrode terminals 13 to 18, respectively (see FIG. 1). Specifically, element contact portions located at forward end portions of the terminal members are in elastic contact with the electrode terminals 13 to 18, respectively. For example, an element contact portion 75b of the terminal member 75 is in elastic contact with and is thus electrically connected to the electrode terminal 14. Also, an element contact portion 76b of the terminal member 76 is in elastic contact with and is thus electrically connected to the electrode terminal 17 (see FIG. 1).

Furthermore, lead wires 71 are electrically connected to the six terminal members (terminal members 75, 76, etc.), respectively. Specifically, a lead wire crimp portion located at a rear end of each terminal member is crimped to a core wire of the lead wire 71, whereby the lead wire 71 is electrically connected to the terminal member. For example, as shown in FIG. 1, a lead wire crimp portion 77 of the terminal member 75 is crimped to a core wire of the lead wire 71, whereby the lead wire 71 is electrically connected to the terminal member 75. Also, a lead wire crimp portion 78 of the terminal member 76 is crimped to a core wire of another lead wire 71, whereby the lead wire 71 is electrically connected to the terminal member 76.

The metallic shell 20 is a tubular member having a through hole 23 extending therethrough in the direction of the axial line AX. The metallic shell 20 has a ledge 25 protruding radially inward and partially constituting the through hole 23. The metallic shell 20 holds the gas sensor element 10 in the through hole 23 while allowing a forward end portion 10s of the gas sensor element 10 to protrude outward (downward in FIG. 1) from its forward end and allowing a rear end portion 10k of the gas sensor element 10 to protrude outward (upward in FIG. 1) from its rear end.

The through hole 23 of the metallic shell 20 accommodates an annular ceramic holder 42, two talc rings 43 and 44 formed by an annularly charged talc powder, and a ceramic sleeve 45. More specifically, the ceramic holder 42, the talc rings 43 and 44, and the ceramic sleeve 45 are stacked in this order from the axially forward side (the lower side in FIG. 1) to the axially rear side (the upper side in FIG. 1) such that they surround the gas sensor element 10.

Also, a metal cup 41 is disposed between the ceramic holder 42 and the ledge 25 of the metallic shell 20. A crimp ring 46 is disposed between the ceramic sleeve 45 and a crimped portion 22 of the metallic shell 20. The crimped portion 22 of the metallic shell 20 is crimped so as to press the ceramic sleeve 45 forward through the crimp ring 46.

An outer protector 31 and an inner protector 32 which are made of metal (specifically, stainless steel) and have a plurality of holes are welded to a forward end portion 20b of the metallic shell 20 so as to cover the forward end portion 10s of the gas sensor element 10. Meanwhile, a tubular casing 51 is welded to a rear end portion of the metallic shell 20. The tubular casing 51 extends in the direction of the axial line AX and surrounds the gas sensor element 10.

The holding member 60 is a tubular member formed of an electrically insulating material (specifically, alumina) and having the insertion hole 62 extending therethrough in the direction of the axial line AX. The aforementioned six terminal members (terminal members 75, 76, etc.) are disposed in the insertion hole 62 (see FIG. 1). The holding member 60 has a collar portion 65 formed at its rear end portion and protruding radially outward. The holding member 60 is held by an internal support member 53 in such a manner that the collar portion 65 is in contact with the internal support member 53. The internal support member 53 is held to the tubular housing 51 by means of a crimped portion 51g of the tubular housing 51 being crimped radially inward.

An insulating member 90 is disposed on a rear end surface 61 of the holding member 60. The insulating member 90 is formed of an electrically insulating material (specifically, alumina) and has a cylindrical shape. The insulating member 90 has six through holes 91 extending therethrough in the direction of the axial line AX. The lead wire crimp portions (lead wire crimp portions 77, 78, etc.) of the terminal members are disposed in the through holes 91, respectively.

An elastic seal member 73 formed of fluororubber is disposed radially inward of a rear end opening portion 51c located at an axially rear end portion (an upper end portion in FIG. 1) of the tubular housing 51 (see FIG. 1). The elastic seal member 73 has six cylindrical insertion holes 73c extending therethrough in the direction of the axial line AX. The insertion holes 73c are formed of insertion hole surfaces 73b (cylindrical inner wall surfaces), respectively, of the elastic seal member 73. The lead wires 71 are inserted through the insertion holes 73c in one-to-one relation. The lead wires 71 extend to the outside of the gas sensor 1 through the insertion holes 73c of the elastic seal member 73. The elastic seal member 73 is radially deformed in an elastically compressive manner through radially inward crimping of the rear end opening portion 51c of the tubular housing 51, whereby the insertion hole surfaces 73b and corresponding outer circumferential surfaces 71b of the lead wires 71 are brought into close contact with one another, thereby establishing a watertight seal between the insertion hole surfaces 73b and the corresponding outer circumferential surfaces 71b of the lead wires 71.

Meanwhile, as shown in FIG. 3, the gas sensor element 10 includes platelike solid electrolyte bodies 111, 121, 131 and insulators 140 and 145 disposed between the solid electrolyte bodies 111, 121, and 131 and has a structure in which these members are laminated in the laminating direction (vertical direction in FIG. 3). Furthermore, the gas sensor element 10 includes a heater 161 laminated on a back surface 131c (lower surface in FIG. 3) of the solid electrolyte body 131. The heater 161 includes platelike insulators 162 and 163 formed primarily of alumina and a heater pattern 164 (formed primarily of Pt) embedded between the insulators 162 and 163 (see FIGS. 3 and 6). The heater pattern 164 includes a heat generating portion 164d in the form of a curved line and rectilinear first and second lead portions 164b and 164c connected to opposite ends, respectively, of the heat generating portion 164d. The first lead portion 164b is electrically connected to the electrode terminal 16, and the second lead portion 164c is electrically connected to the electrode terminal 18 (see FIG. 6).

The solid electrolyte bodies 111, 121, and 131 are formed of zirconia, which is a solid electrolyte, and has oxygen ion conductivity. A porous Ip1 positive electrode 112 is provided on a side toward a front surface 111b (a side toward an upper surface in FIG. 3) of the solid electrolyte body 111. A porous Ip1 negative electrode 113 is provided on a side toward a back surface 111c (a side toward a lower surface in FIG. 3) of the solid electrolyte body 111. The Ip1 positive electrode 112 and the Ip1 negative electrode 113 are formed of cermet which contains Pt powder and ceramic powder, and have gas permeability and water permeability.

In the present embodiment, the Ip1 positive electrode 112 and the Ip1 negative electrode 113 are formed as follows. First, 100 parts by weight Pt powder, 14 parts by weight ceramic powder, and 10 parts by weight organic binder (e.g., ethyl cellulose) are mixed. To the resultant mixture, solvent is added in a predetermined amount, yielding electrode paste. Next, the electrode paste is applied to the side toward the front surface 111b and the side toward the back surface 111c of the solid electrolyte body 111. Subsequently, the organic binder is dissipated through application of heat, thereby forming the porous electrodes 112 and 113.

As shown in FIG. 5, an Ip1 positive lead 116 is connected to a connection portion 112d of the Ip1 positive electrode 112. The Ip1 positive lead 116 is electrically connected to the electrode terminal 13. An Ip1 negative lead 117 is connected to a connection portion 113d of the Ip1 negative electrode 113. The Ip1 negative lead 117 is electrically connected to the electrode terminal 15. The Ip1 positive lead 116 and the Ip1 negative lead 117 are formed of cermet which contains Pt powder and ceramic powder, but are formed to be dense in contrast to the Ip1 positive electrode 112 and the Ip1 negative electrode 113. Thus, the Ip1 positive lead 116 and the Ip1 negative lead 117 are water-impermeable.

In the present embodiment, the Ip1 positive lead 116 and the Ip1 negative lead 117 are formed as follows. First, 100 parts by weight Pt powder, 18 parts by weight ceramic powder, and 5 parts by weight organic binder (e.g., ethyl cellulose) are mixed. To the resultant mixture, solvent is added in a predetermined amount, yielding a lead paste. Next, the lead paste is applied to the side toward the front surface 111b and the side toward the back surface 111c of the solid electrolyte body 111. Subsequently, the organic binder is dissipated through application of heat, thereby forming the leads 116 and 117.

Meanwhile, as compared with the electrode paste, the lead paste contains a reduced (approximately halved) amount of organic binder. By reducing the amount of organic binder, which forms internal pores by dissipation as a result of application of heat, the dense leads 116 and 117 having few internal pores are formed.

A protection layer 115 formed of alumina or the like is laminated on the front side (upper side in FIGS. 3 to 5) of the Ip1 positive electrode 112 and the Ip1 positive lead 116. A first porous body 114 (corresponding to the porous body of the invention) is formed in the protection layer 115 so as to face the Ip1 positive electrode 112 in the laminating direction and is exposed to an ambient atmosphere of the gas sensor element 10. The first porous body 114 has gas permeability and water permeability and is in contact with a portion of the Ip1 positive electrode 112. That portion of the Ip1 positive electrode 112 which is in contact with the first porous body 114 is a porous body contact portion 112b.

The solid electrolyte body 111 and the electrodes 112 and 113 constitute an Ip1 cell 110 (first pump cell) (see FIG. 3). The Ip1 cell 110 pumps oxygen (so-called oxygen pumping) between an atmosphere in contact with the electrode 112 (ambient atmosphere of the gas sensor element 10) and an atmosphere in contact with the electrode 113 (atmosphere within a first measuring chamber 150, described below) according to a pump current Ip1 applied between the electrodes 112 and 113.

The solid electrolyte body 121 is disposed so as to face the solid electrolyte body 111 in the laminating direction with the insulator 140 intervening therebetween. A porous Vs negative electrode 122 is provided on a side toward a front surface 121b (a side toward an upper surface in FIG. 3) of the solid electrolyte body 121. A porous Vs positive electrode 123 is provided on a side toward a back surface 121c (a side toward a lower surface in FIG. 3) of the solid electrolyte body 121. The Vs negative electrode 122 and the Vs positive electrode 123 are formed of cermet which contains Pt powder and ceramic powder, and have gas permeability and water permeability.

As shown in FIG. 5, a Vs negative lead 126 is connected to a connection portion 122d of the Vs negative electrode 122. The Vs negative lead 126 is electrically connected to the electrode terminal 15. The Vs negative lead 126 is formed of cermet which contains Pt powder and ceramic powder, but is formed to be dense in contrast to the Vs negative electrode 122. Thus, the Vs negative lead 126 is water-impermeable. Meanwhile, as shown in FIGS. 5 and 6, a Vs positive lead 127 is connected to a connection portion 123d of the Vs positive lead 127. The Vs positive lead 127 is electrically connected to an electrode terminal portion 14. The Vs positive lead 127 is formed of cermet which contains Pt powder and ceramic powder, but is formed porously. This is because the Vs positive lead 127 is formed simultaneously with the Vs positive electrode 123. Thus, the Vs positive lead 127 has gas permeability and water permeability.

The first measuring chamber 150, which is an internal space, is formed between the solid electrolyte body 111 and the solid electrolyte body 121 (see FIG. 3). The first measuring chamber 150 is an internal space of the gas sensor element 10 into which exhaust gas that flows through an exhaust path is first introduced, and communicates with the ambient atmosphere of the gas sensor element 10 through a second porous body 151 having gas permeability and water permeability. The second porous body 151 is provided laterally of the first measuring chamber 150 as a partition between the first measuring chamber 150 and the ambient atmosphere of the gas sensor element 10. The second porous body 151 limits the amount of inflow per unit time of exhaust gas into the first measuring chamber 150 (see FIGS. 2 and 5).

A third porous body 152 is provided at the rear side (right side in FIG. 3) of the first measuring chamber 150 as a partition between the first measuring chamber 150 and a second measuring chamber 160, described below. The third porous body 152 limits the amount of flow per unit time of exhaust gas.

The solid electrolyte body 121 and the electrodes 122 and 123 constitute a Vs cell 120 (see FIG. 3). The Vs cell 120 mainly generates an electromotive force according to a difference in partial pressure of oxygen between two atmospheres (an atmosphere within the first measuring chamber 150 in contact with the electrode 122 and an atmosphere within a reference oxygen chamber 170 in contact with the electrode 123) separated by the solid electrolyte body 121.

The solid electrolyte body 131 is disposed so as to face the solid electrolyte body 121 in the laminating direction with the insulator 145 sandwiched therebetween. A porous Ip2 positive electrode 132 and a porous Ip2 negative electrode 133 are provided on a side toward a front surface 131b (a side toward an upper surface in FIG. 3) of the solid electrolyte body 131. The Ip2 positive electrode 132 and the Ip2 negative electrode 133 are formed of cermet which contains Pt powder and ceramic powder, and has gas permeability and water permeability.

As shown in FIG. 6, an Ip2 positive lead 136 is connected to the Ip2 positive electrode 132. The Ip2 positive lead 136 is electrically connected to the electrode terminal 17. The Ip2 positive lead 136 is formed of cermet which contains Pt powder and ceramic powder, but is formed porously. This is because the Ip2 positive lead 136 is formed simultaneously with the Ip2 positive electrode 132. Thus, the Ip2 positive lead 136 has gas permeability and water permeability. Meanwhile, an Ip2 negative lead 137 is connected to a connection portion 133d of the Ip2 negative electrode 133. The Ip2 negative lead 137 is electrically connected to the electrode terminal 15. The Ip2 negative lead 137 is formed of cermet which contains Pt powder and ceramic powder, but is formed to be dense in contrast to the Ip2 negative electrode 133. Thus, the Ip2 negative lead 137 is water-impermeable.

A reference oxygen chamber 170, which is an isolated small space, is formed between the Ip2 positive electrode 132 and the Vs positive electrode 123 (see FIG. 3). The reference oxygen chamber 170 is an opening 145b formed in the insulator 145. In the reference oxygen chamber 170, a porous body made of ceramic is disposed at a side toward the Ip2 positive electrode 132.

Also, a second measuring chamber 160, which is an internal space of the gas sensor element, is formed so as to face the Ip2 negative electrode 133 in the laminating direction. The second measuring chamber 160 is defined by an opening 145c extending through the insulator 145 in the laminating direction, an opening 125 extending through the solid electrolyte body 121 in the laminating direction, and an opening 141 extending through the insulator 140 in the laminating direction.

The first measuring chamber 150 and the second measuring chamber 160 communicate with each other through the third porous body 152 having gas permeability and water permeability. Therefore, the second measuring chamber 160 communicates with the ambient atmosphere of the gas sensor element 10 through the second porous body 151, the first measuring chamber 150 and the third porous body 152.

In the present embodiment, the first measuring chamber 150 and the second measuring chamber 160 correspond to "an internal space of the gas sensor element, the internal space communicating with an ambient atmosphere of the gas sensor element" of the invention.

The solid electrolyte body 131 and the electrodes 132 and 133 constitute an Ip2 cell 130 (second pump cell) for detecting $NO_x$ concentration. The Ip2 cell 130 moves oxygen (oxygen ions) formed by decomposition of $NO_x$ decomposed in the second measuring chamber 160, to the reference oxygen chamber 170 through the solid electrolyte body 131. At this time, electric current flows through the lead 136 connected to the electrode 132 and through the lead 137 connected to the electrode 133, according to $NO_x$ concentration of the exhaust gas (gas to be measured) introduced into the second measuring chamber 160.

In the present embodiment, an alumina insulation layer 118 is formed on the front surface 111b of the solid electrolyte body 111. Furthermore, the Ip1 positive lead 116 and a portion of the Ip1 positive electrode 112 are formed on the alumina insulation layer 118. Furthermore, the porous body contact portion 112b of the Ip1 positive electrode 112 has an electrolyte body contact portion 112c which is in contact with the solid electrolyte body 111 by means of a through hole 118b extending through the alumina insulation layer 118 in the laminating direction.

Furthermore, an alumina insulation layer 119 is formed on the back surface 111c of the solid electrolyte body 111. Also, the Ip1 negative lead 117 and a portion of the Ip1 negative electrode 113 are formed on the alumina insulation layer 119. Furthermore, that space exposure portion 113b of the Ip1 negative electrode 113 which is exposed to the first measuring chamber 150 (internal space) has an electrolyte body contact portion 113c which is in contact with the solid electrolyte body 111 by means of a through hole 119b extending through the alumina insulation layer 119 in the laminating direction.

Furthermore, in the present embodiment, an alumina insulation layer 128 is formed on the front surface 121b of the solid electrolyte body 121. Also, the Vs negative lead 126 and a portion of the Vs negative electrode 122 are formed on the alumina insulation layer 128. Furthermore, that space exposure portion 122b of the Vs negative electrode 122 which is exposed to the first measuring chamber 150 (internal space) has an electrolyte body contact portion 122c which is in contact with the solid electrolyte body 121 by means of a through hole 128b extending through the alumina insulation layer 128 in the laminating direction.

Furthermore, an alumina insulation layer 129 is formed on the back surface 121c of the solid electrolyte body 121. Also, the Vs positive lead 127 and a portion of the Vs positive electrode 123 are formed on the alumina insulation layer 129. Furthermore, the Vs positive electrode 123 has an electrolyte body contact portion 123c which is in contact with the solid electrolyte body 121 by means of a through hole 129b extending through the alumina insulation layer 129 in the laminating direction.

Furthermore, in the present embodiment, an alumina insulation layer 138 is formed on the front surface 131b of the solid electrolyte body 131. Also, the Ip2 positive lead 136 and a portion of the Ip2 positive electrode 132 are formed on the alumina insulation layer 138. Furthermore, the Ip2 negative lead 137 and a portion of the Ip2 negative electrode 133 are also formed on the alumina insulation layer 138. The electrode 132 has an electrolyte body contact portion 132c which is in contact with the solid electrolyte body 131 by means of a through hole 138b extending through the alumina insulation layer 138 in the laminating direction. Also, that space exposure portion 133b of the electrode 133 which is exposed to the second measuring chamber 160 (internal space) has an electrolyte body contact portion 133c which is in contact with the solid electrolyte body 131 by means of a through hole 138c extending through the alumina insulation layer 138 in the laminating direction.

By employing such a configuration, only the electrolyte body contact portions 112c, 113c, 122c, 123c, 132c and 133c of the electrodes 112, 113, 122, 123, 132 and 133 can function as sensing portions; thus, an object of detection; i.e., gas concentration, can be accurately detected. Notably, since the leads 116, 117, 126 and 137 differ from the electrodes 112, 113, 122 and 133 in electrical characteristics, in a configuration in which leads and connection portions connected to the leads are partially in contact with solid electrolyte, accuracy in detecting gas concentration deteriorates as compared with the present embodiment which does not involve such contact.

In the present embodiment, the Ip1 negative electrode 113, the Vs negative electrode 122, and the Ip2 negative electrode 133 correspond to the "first electrode" of the invention. Furthermore, the Ip1 negative lead 117, the Vs negative lead 126 and the Ip2 negative lead 137 correspond to the "first lead" of the invention. Also, the Ip1 positive electrode 112 corresponds to the "second electrode" of the invention. Furthermore, the Ip1 positive lead 116 corresponds to the "second lead" of the invention.

The connection portion 112d of the Ip1 positive electrode 112 (second electrode) is disposed away from the first porous body 114 with respect to a planar direction (horizontal direction in FIGS. 3 and 5) orthogonal to the laminating direction, and is connected to the Ip1 positive lead 116 (second lead). Moreover, the connection portion 112d is a portion of the Ip1 positive electrode 112 located most distant from the first porous body 114.

Furthermore, the connection portion 113d of the Ip1 negative electrode 113 (first electrode) is disposed at a position not exposed to the first measuring chamber 150 (internal space) and is connected to the Ip1 negative lead 117 externally of the first measuring chamber 150. Also, the connection portion 113d is a portion of the Ip1 negative electrode 113 located most distant from the first measuring chamber 150. Similarly, the connection portion 122d of the Vs negative electrode 122 is also disposed at a position not exposed to the first measuring chamber 150 (internal space) and is connected to the Vs negative lead 126 externally of the first measuring chamber 150. Moreover, the connection portion 122d is a portion of the Vs negative electrode 122 located most distant from the first measuring chamber 150.

Also, the connection portion 133d of the Ip2 negative electrode 133 is disposed at a position not exposed to the second measuring chamber 160 (internal space) and is connected to the Ip2 negative lead 137 externally of the second measuring chamber 160. Moreover, the connection portion 133d is a portion of the Ip2 negative electrode 133 located most distant from the second measuring chamber 160.

In the present embodiment, the connection portion 112d of the Ip1 positive electrode 112 corresponds to the "second connection portion" of the invention. Also, the connection portion 113d of the Ip1 negative electrode 113, the connection portion 122d of the Vs negative electrode 122, and the connection portion 133d of the Ip2 negative electrode 133 correspond to the "first connection portion" of the invention.

As described above, in the present embodiment, the connection portions 113d, 122d and 133d (first connection portion) are connected to the Ip1 negative lead 117, the Vs negative lead 126 and Ip2 negative lead 137 (first lead) at positions not exposed to the first measuring chamber 150 and the second measuring chamber 160 (internal space).

Thus, in contrast to Patent Document 1 (Japanese Patent No. 4165652) discussed above, "deterioration in accuracy in detecting a concentration of oxygen or a concentration of $NO_x$ in gas to be measured, as a result of deterioration in oxygen pumping performance stemming from disposition of the first connection portion within the internal space" can be restrained.

Furthermore, the connection portion 112d (second connection portion) is connected to the Ip1 positive lead 116 (second lead) at a position which is located away from the first porous body 114 with respect to a planar direction (horizontal direction in FIGS. 3 and 5). Thus, "deterioration in accuracy in detecting a concentration of oxygen or a concentration of $NO_x$ in gas to be measured, as a result of deterioration in oxygen pumping performance stemming from disposition of the second connection portion at such a position as to overlap the porous body" can be restrained.

Detection of $NO_x$ concentration by the gas sensor 1 of the present embodiment will be described briefly. As the heater pattern 164 rises in temperature, the solid electrolyte bodies 111, 121 and 131 of the gas sensor element 10 are heated and activated. This initiates operation of the Ip1 cell 110, the Vs cell 120 and the Ip2 cell 130.

Exhaust gas (gas to be measured) which flows through an exhaust path (not shown) is introduced into the first measuring chamber 150 while being limited in flow rate by the second porous body 151. At this time, a weak current Icp is applied to the Vs cell 120 and flows from the electrode 123 to the electrode 122. Thus, oxygen contained in exhaust gas can receive electrons from the electrode 122, which is a negative electrode, within the first measuring chamber 150 and become oxygen ions. The oxygen ions flow through the solid electrolyte body 121 and move into the reference oxygen chamber 170. That is, as a result of applying the current Icp between electrodes 122 and 123, oxygen in the first measuring chamber 150 is moved to the reference oxygen chamber 170.

In the case where the oxygen concentration of exhaust gas introduced into the first measuring chamber 150 is lower than a predetermined value, the current Ip1 is applied to the Ip1 cell 110 so that the electrode 112 becomes a negative electrode. As a result, oxygen is pumped into the first measuring chamber 150 from the ambient atmosphere of the gas sensor element 10. By contrast, in the case where the oxygen concentration of exhaust gas introduced into the first measuring chamber 150 is higher than a predetermined value, the current Ip1 is applied to the Ip1 cell 110 so that the electrode 113 becomes a negative electrode. As a result, oxygen is pumped from inside the first measuring chamber 150 to the ambient atmosphere of the gas sensor element 10.

Exhaust gas whose oxygen concentration has been adjusted as described above in the first measuring chamber 150 is introduced into the second measuring chamber 160 through the third porous body 152. $NO_x$ contained in exhaust gas comes into contact with the electrode 133 within the second measuring chamber 160 and is decomposed (reduced) on the electrode 133 into nitrogen and oxygen by applying the voltage Vp2 between the electrodes 132 and 133. Oxygen generated by decomposition flows, in the form of oxygen ions, through the solid electrolyte body 131 and moves into the reference oxygen chamber 170. At this time, residual oxygen which has not been pumped out from the first measuring chamber 150 similarly moves into the reference oxygen chamber 170 by operation of the Ip2 cell 130. Thus, current stemming from $NO_x$ and current stemming from residual oxygen flow through the Ip2 cell 130.

Since residual oxygen which has not been pumped out from the first measuring chamber 150 is adjusted in concentration to a predetermined value as described above, current stemming from the residual oxygen can be considered substantially constant and thus has little influence on variation in current stemming from $NO_x$. Thus, current flowing through the Ip2 cell 130 is proportional to $NO_x$ concentration. Therefore, by detecting the current Ip2 which flows through the Ip2 cell 130, a concentration of $NO_x$ in exhaust gas can be detected based on the detected current Ip2.

Meanwhile, a conventional gas sensor element involves a risk of generating cracks therein as a result of freezing water which has penetrated into the first electrode (e.g., the Ip1 negative electrode 113). Specifically, for example, water condensed on the surface of the gas sensor element may penetrate into the internal space of the gas sensor element through the second porous body 151 and further into the first electrode. Water which has penetrated into the first electrode reaches the first connection portion (e.g., the connection portion 113d) connected to the first lead (e.g., the Ip1 negative lead 117) and may stagnate in the first connection portion, since the first lead is water-impermeable. When condensed water stagnating in the first connection portion freezes and thus expands in volume, stress is generated in such a direction as to separate layers between which the first connection portion is sandwiched, potentially generating a crack between the layers (between which the first connection portion is sandwiched) of the gas sensor element.

Figure 7:
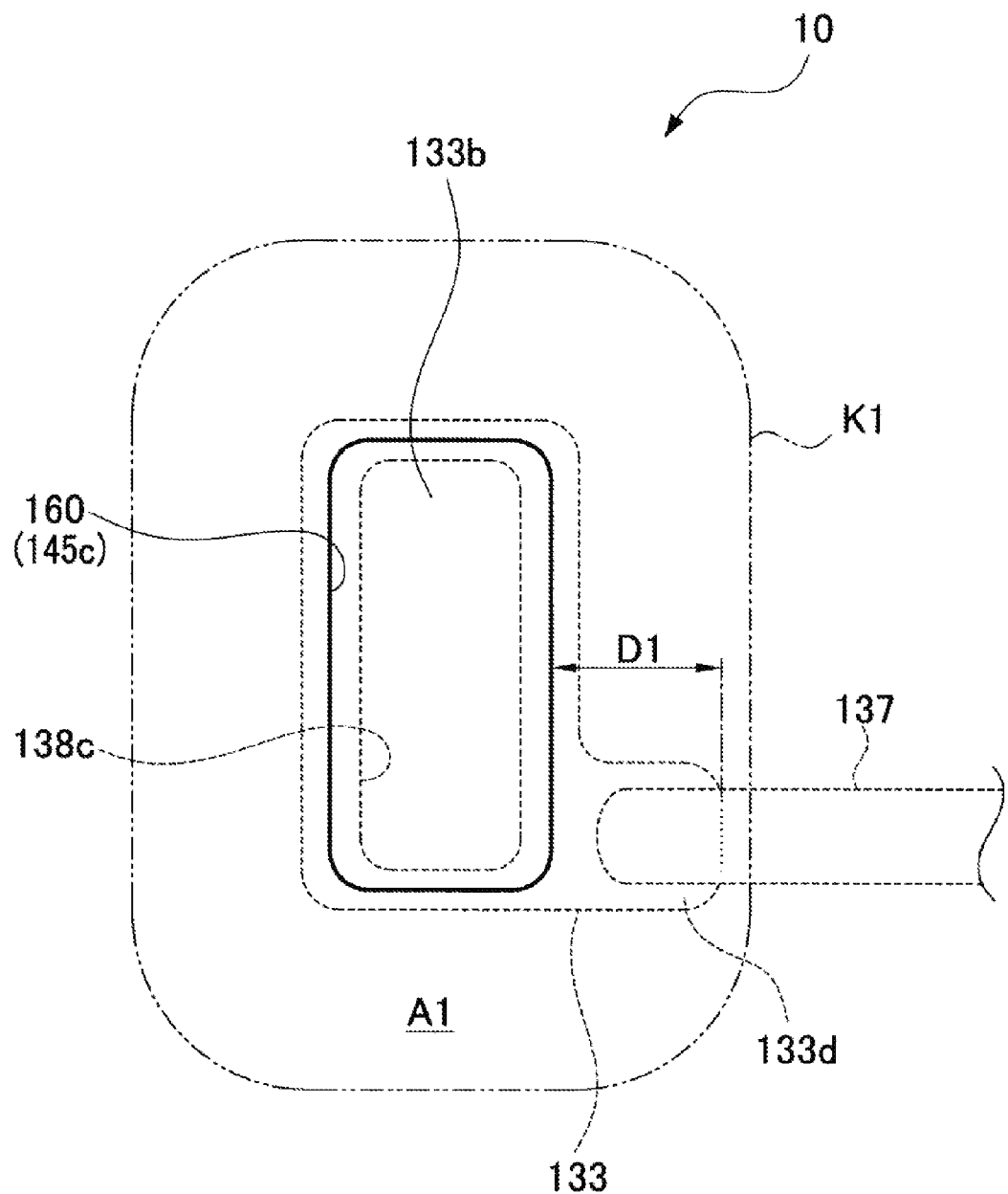
FIG. 7 is a view showing the position of a connection portion of an Ip2 negative electrode as viewed in the direction of arrow C of FIG. 3.

By contrast, in the gas sensor element 10 of the present embodiment, the entirety of the first connection portion (specifically, the connection portions 113d, 122d and 133d) is disposed in a region which extends from the internal space (the first measuring chamber 150 or the second measuring chamber 160) over a distance of 1.0 mm or less. For example, as shown in FIG. 7, the entirety of the connection portion 133d (first connection portion) is disposed inside a region A1 (surrounded by the dash-dot-dot line K1 in FIG. 7) which extends from the second measuring chamber 160 (internal space) over a distance of 1.0 mm or less. Similarly, as for the connection portions 113d and 122d, the entirety thereof is also disposed inside a region which extends from the first measuring chamber 150 (internal space) over a distance of 1.0 mm or less.

Thus, even when water penetrates into the Ip2 negative electrode 133 (first electrode) and then freezes, generation of cracks in the gas sensor element 10 can be prevented. The same applies to the case of penetration of water into the Ip1 negative electrode 113 and into the Vs negative electrode 122. These are apparent from the results of a freezing test, described below. A reason why generation of cracks can be prevented is considered to be as follows.

For example, as water stagnating in the connection portion 133d of the Ip2 negative electrode 133 begins to freeze, pores in the connection portion 133d gradually reduce in volume (ice gradually closes pores). Thus, water stagnating in the connection portion 133d moves in a direction opposite the Ip2 negative lead 137 (first lead) (i.e., toward the second measuring chamber 160 having sufficient space for allowing penetration of water, or leftwards in FIG. 7). At this time, since the entire connection portion 133d is disposed in the region A1 which extends from the second measuring chamber 160 over a distance of 1.0 mm or less (i.e., a short distance D1 of 1.0 mm or less is provided between the second measuring chamber 160 and that portion of the connection portion 133d which is most distant from the second measuring chamber 160), most of the water stagnating in the connection portion 133d can be moved (released) to the second measuring chamber 160 before freezing in the connection portion 133d. Subsequently, even though most water freezes and thus expands within the second measuring chamber 160, no stress is generated in such a direction as to separate the layers of the gas sensor element 10. As a result, generation of cracks in the gas sensor element 10 can be prevented. The same is applied to the case of freezing of water stagnating in the connection portion 113d of the Ip1 negative electrode 113 and in the connection portion 122d of the Vs negative electrode 122.

Also, a conventional gas sensor element involves a risk of generating cracks therein as a result of freezing of water which has penetrated into the second electrode (Ip1 positive electrode 112). Specifically, for example, water condensed on the surface of the gas sensor element may penetrate into the second electrode through the first porous body 114 in contact with the second electrode. Water which has penetrated into the second electrode reaches the second connection portion (connection portion 112d) connected to the second lead (Ip1 positive lead 116) and may stagnate in the second connection portion, since the second lead is water-impermeable. When condensed water stagnating in the second connection portion freezes and thus expands in volume, stress is generated in such a direction as to separate layers between which the second connection portion is sandwiched, potentially generating a crack between the layers (between which the second connection portion is sandwiched) of the gas sensor element.

Figure 8:
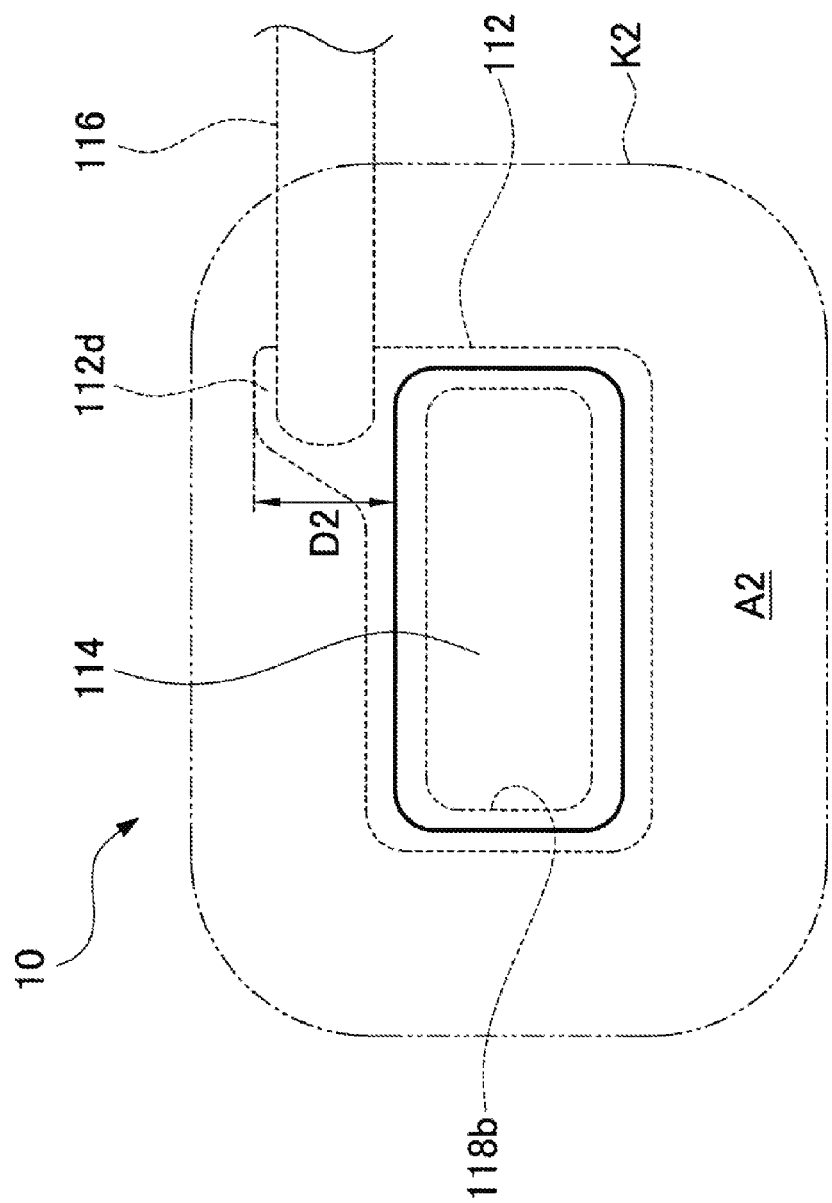
FIG. 8 is a view showing the position of a connection portion of an Ip1 positive electrode as viewed in the direction of arrow G of FIG. 3.

By contrast, in the gas sensor element 10 of the present embodiment, as shown in FIG. 8, the entirety of the connection portion 112d (second connection portion) is disposed inside a region A2 (surrounded by the dash-dot-dot line K2 in FIG. 8) which extends from the first porous body 114 over a distance of 1.0 mm or less. In other words, a distance D2 of 1.0 mm or less is provided between the first porous body 114 and that portion of the connection portion 112d (second connection portion) which is most distant from the first porous body 114. Thus, even when water penetrates into the Ip1 positive electrode 112 (second electrode) and then freezes, generation of cracks in the gas sensor element 10 can be prevented. This is apparent from the results of the freezing test, described below. Therefore, in the gas sensor 1 having the thus-configured gas sensor element 10, even when water penetrates into water-permeable electrodes and then freezes, generation of cracks in the gas sensor element can be prevented, so that gas to be measured can be appropriately detected.

(Freezing Test)

Next a freezing test conducted on gas sensor elements will be described.

Specifically, gas sensor elements (hereinafter, also referred to as test elements) were fabricated which differ in distance D1 between the internal space (the first measuring chamber 150 or the second measuring chamber 160) and that portion of the first connection portion (the connection portions 113d and 122d or the connection portion 133d) which is located most distant from the internal space and in distance D2 between the second porous body and that portion of the second connection portion (the connection portion 112d) which is located most distant from the second porous body. Twenty gas sensor elements were fabricated for each value of D1 and D2. The distances D1 and D2 were varied from 0 mm to 2.0 mm at 0.2 mm intervals for the connection portions.

Next, the freezing test was conducted on the fabricated test elements.

Specifically, first, forward end portions (including the second porous bodies 151 and the first porous bodies 114) of the test elements were immersed in water and allowed to stand for 24 hours in the immersed condition. This procedure allowed water to penetrate into the test elements (the electrodes 112, 113, 122 and 133) through the second porous bodies 151 and through the first porous bodies 114. Next, the test elements were taken out of the water, and water adhering to the surfaces of the test elements was wiped off. Then, the test elements were placed in a thermostatic chamber whose inner temperature was set to −20° C. and then allowed to stand for two minutes. By this procedure, water which had penetrated into the test elements was frozen. Subsequently, the test elements were taken out from the thermostatic chamber and were then allowed to stand at room temperature for one minute. This cycle of allowing the test elements to stand in the thermostatic chamber and then allowing the test elements to stand at room temperature was repeated ten times. Subsequently, a red liquid was applied to the surfaces of the test elements. After a predetermined time elapsed subsequent to application of the red liquid, the applied red liquid was wiped off from the surfaces of the test elements. The wiped surfaces of the test elements were checked for appearance to check for the generation of cracks.

Figure 9:
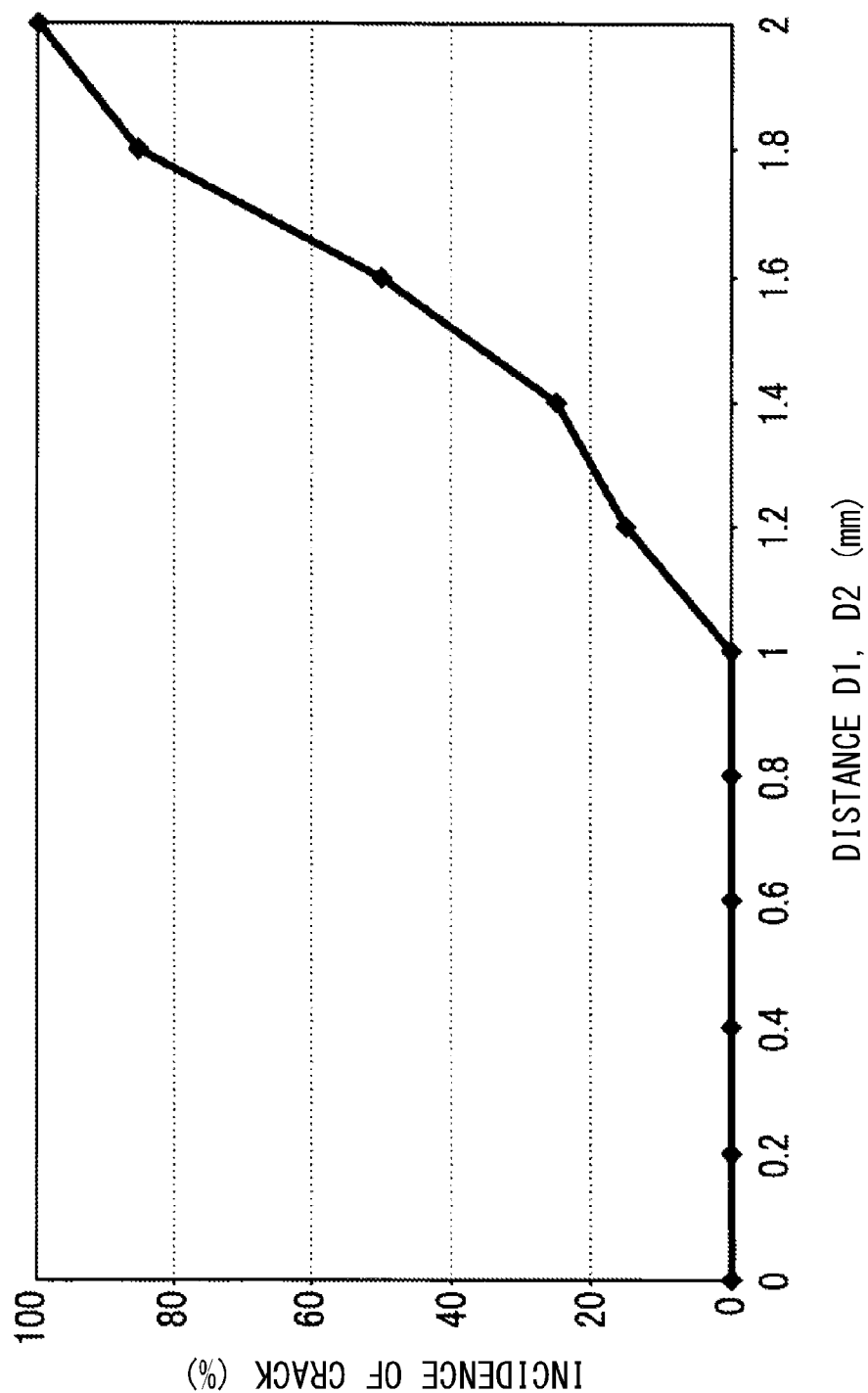
FIG. 9 shows a correlation diagram between the incidence of cracking and distances D1 and D2.

Specifically, since the red liquid penetrates into any cracks that are present, the red liquid remains even after the surface of a test element is wiped. Therefore, in the case of generation of cracks in layers between which the first connection portion (the connection portions 113d and 122d or the connection portion 133d) and the second connection portion (the connection portion 112d) are sandwiched, the red liquid remains between the layers. On the basis of this test, a judgment was made as to whether or not cracks were generated. FIG. 9 shows the results of this evaluation.

As shown in FIG. 9, the gas sensor elements having a distance D1 of 1.0 mm or less were free of generation of cracks. Similarly, the gas sensor elements having a distance D2 of 1.0 mm or less were free of generation of cracks.

By contrast, some gas sensor elements having a distance D1 of greater than 1.0 mm suffered generation of cracks. Specifically, in the case of setting a distance D1 of 1.2 mm, the incidence of cracking was 15%. That is, three test elements out of twenty test elements exhibited generation of cracks. Also, in the case of setting a distance D1 of 1.4 mm, the incidence of cracking was 25%. That is, five test elements out of twenty test elements exhibited generation of cracks. In the case of setting a distance D1 of 1.6 mm, the incidence of cracking was 50%. That is, ten test elements out of twenty test elements exhibited generation of cracks. In the case of setting a distance D1 of 1.8 mm, the incidence of cracking was 85%. That is, seventeen test elements out of twenty test elements exhibited generation of cracks. In the case of setting a distance D1 of 2.0 mm, the incidence of cracking was 100%. That is, all of twenty test elements exhibited generation of cracks.

Also, in the case of setting a distance D2 of greater than 1.0 mm, some gas sensor elements exhibited generation of cracks. The incidence of cracking was equivalent to that in the case of the distance D1 (see FIG. 9).

From the above-described test results, the following was determined: by disposing the entirety of the connection portions 113d and 122d (first connection portion) in a region which extends from the first measuring chamber 150 (internal space) over a distance of 1.0 mm or less, even when water penetrates into the electrodes 113 and 122 and then freezes, the generation of a crack between the layers between which the connection portions 113d and 122d are sandwiched can be prevented. Furthermore, the following was determined: by disposing the entirety of the connection portion 133d (first connection portion) in a region which extends from the second measuring chamber 160 (internal space) over a distance of 1.0 mm or less, even when water penetrates into the electrode 133 and then freezes, the generation of a crack between the layers between which the connection portion 133d is sandwiched can be prevented. Also, the following was determined: by disposing the entirety of the connection portion 112d (second connection portion) in a region which extends from the first porous body 114 over a distance of 1.0 mm or less, even when water penetrates into the electrode 112 and then freezes, generation of a crack between the layers between which the connection portion 112d is sandwiched can be prevented.

Modified Embodiment

Next, a modified embodiment of the present invention will be described. A gas sensor 201 of the modified embodiment differs from the gas sensor 1 of the embodiment only in the gas sensor element and is similar in other respects (see FIG. 1). Therefore, features different from those of the embodiment will be described, and description of similar features will be omitted or simplified.

In the gas sensor element 10 of the embodiment, as shown in FIG. 7, the entirety of the connection portion 133d (first connection portion) of the Ip2 negative electrode 133 is disposed inside the region A1 (surrounded by the dash-dot-dot line K1 in FIG. 7) which extends from the second measuring chamber 160 (internal space) over a distance of 1.0 mm or less.

Figure 10:
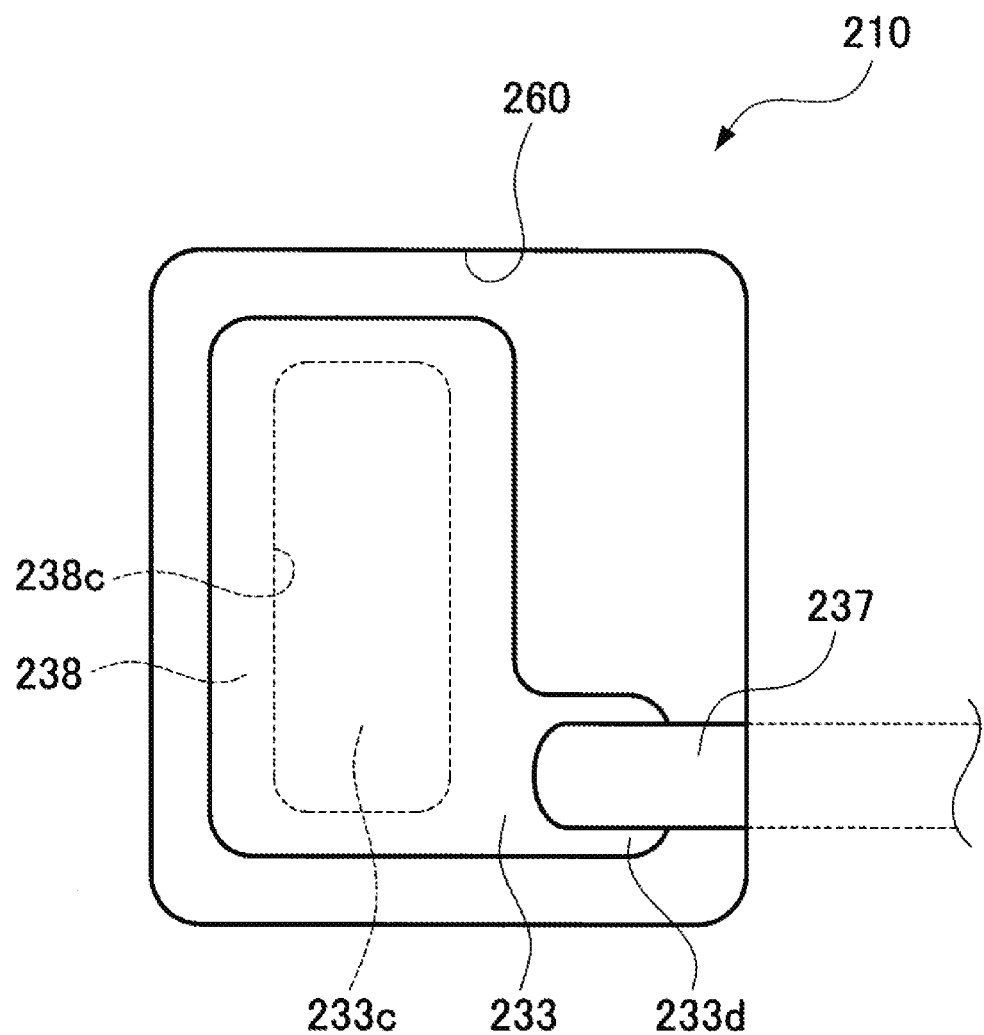
FIG. 10 is a view showing the position of a connection portion of an Ip2 negative electrode of a gas sensor element according to a modified embodiment.

By contrast, in a gas sensor element 210 of the present modified embodiment, as shown in FIG. 10, an Ip2 negative electrode 233 is disposed within a second measuring chamber 260 (internal space). That is, the entirety of the Ip2 negative electrode 233 including a connection portion 233d is disposed within the second measuring chamber 260 (internal space). Thus, the entirety of the Ip2 negative electrode 233 including the connection portion 233d is exposed to the second measuring chamber 260 (internal space). Also, an Ip2 negative lead 237 is connected to the connection portion 233d of the Ip2 negative electrode 233 at a position within the second measuring chamber 260 (internal space).

By employing such a configuration, even when water penetrates into the Ip2 negative electrode 233 and then freezes, the generation of cracks in the gas sensor element can be prevented. Since the entirety of the Ip2 negative electrode 233 (third electrode) including the connection portion 233d is disposed within the second measuring chamber 260 (internal space), water stagnating in the Ip2 negative electrode 233 including the connection portion 233d (third connection portion) can be frozen (expanded) within the second measuring chamber 260; as a result, the generation of stress in such a direction as to separate the layers of the gas sensor element can be restrained.

Also, the Ip2 negative electrode 233 has an electrolyte body contact portion 233c which is in contact with the solid electrolyte body 131 by means of a through hole 238c formed in the alumina insulation layer 238 formed on the solid electrolyte body 131 (see FIG. 10). Meanwhile, the Ip2 negative lead 237 is formed on the alumina insulation layer 238 (thus not in contact with the solid electrolyte body 131). The connection portion 233d of the Ip2 negative electrode 233 is connected to the Ip2 negative lead 237 on the alumina insulation layer 238 (and is thus not in contact with the solid electrolyte body 131). Therefore, although the connection portion 233d is disposed within the second measuring chamber 260 (internal space), the connection portion 233d does not affect oxygen pumping performance of the Ip2 negative electrode 233 (the connection portion 233d does not deteriorate oxygen pumping performance of the Ip2 negative electrode 233). Thus, deterioration in accuracy in detecting a concentration of oxygen or a concentration of $NO_x$ in a gas to be measured can be restrained. Furthermore, only the electrolyte body contact portion 233c of the Ip2 negative electrode 233 can function as a sensing portion. Thus, an object of detection; i.e., gas concentration, can be accurately detected.

In the present modified embodiment, the Ip2 negative electrode 233 corresponds to the "third electrode" of the invention. The connection portion 233d corresponds to the "third connection portion" of the invention. The Ip2 negative lead 237 corresponds to the "third lead" of the invention. The alumina insulation layer 238 corresponds to the "third insulation layer" of the invention. The electrolyte body contact portion 233c corresponds to the "third electrolyte body contact portion" of the invention.

As for the Ip1 negative electrode and the Vs negative electrode, similar to the case of the Ip2 negative electrode 233, by disposing the entirety of the electrode including the connection portion connected to the leads within the first measuring chamber (internal space), generation of cracks can be restrained.

Also, in the gas sensor element 10 of the embodiment, as shown in FIG. 8, the entirety of the connection portion 112d (second connection portion) of the Ip1 positive electrode 112 is disposed in the region A2 (surrounded by the dash-dot-dot line K2 in FIG. 8) which extends from the first porous body 114 over a distance of 1.0 mm or less.

Figure 11:
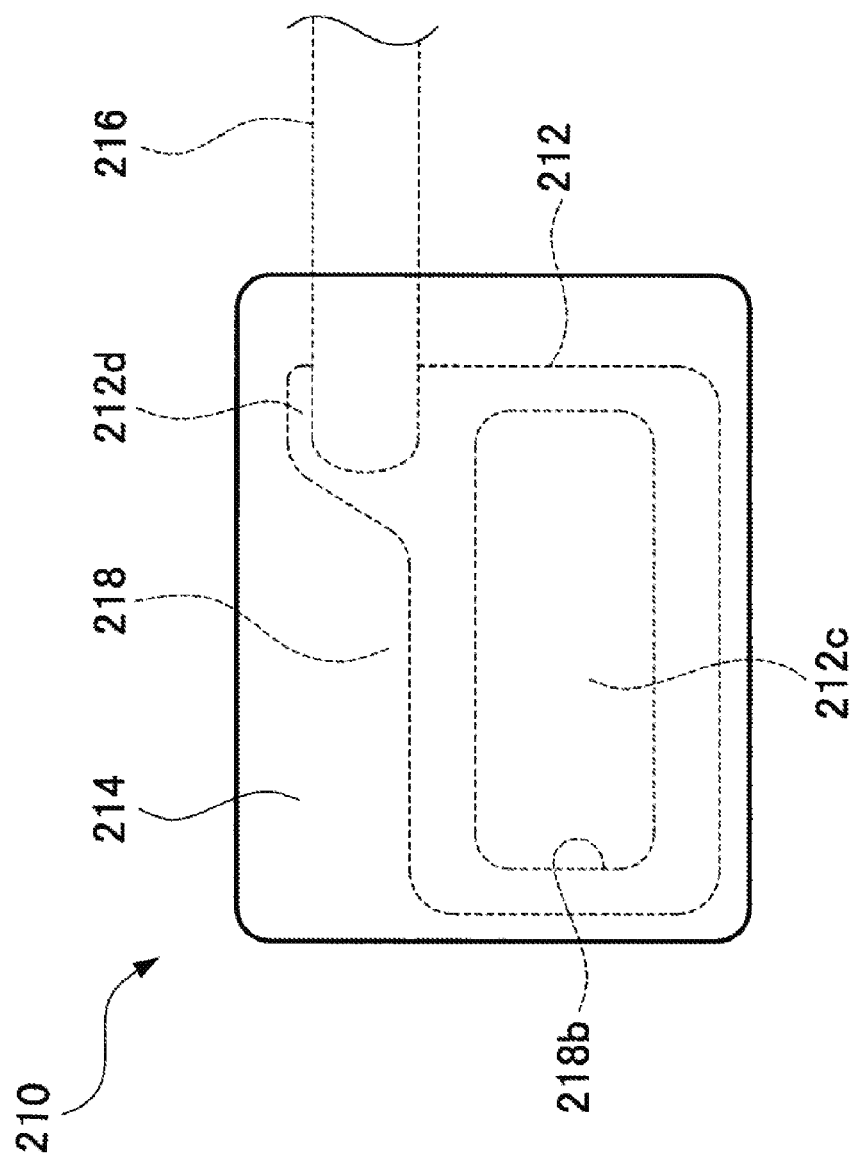
FIG. 11 is a view showing the position of a connection portion of an Ip1 positive electrode of the gas sensor element according to the modified embodiment.

By contrast, in the gas sensor element 210 of the present modified embodiment, as shown in FIG. 11, while an Ip1 positive electrode 212 is in contact with a first porous body 214, the entirety of the Ip1 positive electrode 212 is disposed so as to face the first porous body 214 with respect to the laminating direction of electrolyte bodies (the thickness direction; i.e., a direction orthogonal to the page on which FIG. 11 appears). More specifically, the entirety of the Ip1 positive electrode 212 faces the first porous body 214 such that a portion of the Ip1 positive electrode 212 faces the first porous body 214 with an Ip1 positive lead 216 sandwiched therebetween and such that the remaining portion (a portion free of the lead 216 with respect to the laminating direction) is in contact with the first porous body 214. The Ip1 positive lead 216 is connected to a connection portion 212d of the Ip1 positive electrode 212 so as to face the first porous body 214 with respect to the laminating direction.

By employing such a configuration, even when water penetrates into the Ip1 positive electrode 212 and then freezes, the generation of cracks in the gas sensor element can be prevented. Since the entirety of the Ip1 positive electrode 212 including the connection portion 212d is disposed so as to face the first porous body 214, and most of the electrode 212 excluding a portion in contact with the Ip1 positive lead 216 is in contact with the first porous body 214, most of water stagnating in the Ip1 positive electrode 212 can be frozen (expanded) within pores of the first porous body 214; as a result, generation of stress in such a direction as to separate the layers of the gas sensor element can be restrained.

Also, the Ip1 positive electrode 212 has an electrolyte body contact portion 212c which is in contact with the solid electrolyte body 111 by means of a through hole 218b formed in an alumina insulation layer 218 formed on the solid electrolyte body 111 (see FIG. 11). Meanwhile, the Ip1 positive lead 216 is formed on the alumina insulation layer 218 (and thus is not in contact with the solid electrolyte body 111). The connection portion 212d of the Ip1 positive electrode 212 is connected to the Ip1 positive lead 216 on the alumina insulation layer 218 (and thus is not in contact with the solid electrolyte body 111). Therefore, although the connection portion 212d (fourth connection portion) is disposed so as to overlap the first porous body 214 (at such a position as to face the first porous body 214 with respect to the laminating direction), the connection portion 212d does not affect oxygen pumping performance of the Ip1 positive electrode 212 (fourth electrode) (the connection portion 212d does not deteriorate oxygen pumping performance of the Ip1 positive electrode 212). Thus, deterioration in accuracy in detecting a concentration of oxygen or a concentration of $NO_x$ in a gas to be measured can be restrained. Furthermore, only the electrolyte body contact portion 212c of the Ip1 positive electrode 212 can function as a sensing portion. Thus, an object of detection; i.e., gas concentration, can be accurately detected.

In the present modified embodiment, the Ip1 positive electrode 212 corresponds to the "fourth electrode" of the invention. The connection portion 212d corresponds to the "fourth connection portion" of the invention. The Ip1 positive lead 216 corresponds to the "fourth lead" of the invention. The alumina insulation layer 218 corresponds to the "fourth insulation layer" of the invention. The electrolyte body contact portion 212c corresponds to the "fourth electrolyte body contact portion" of the invention.

While the present invention has been described with reference to the embodiment and the modified embodiment, the present invention is not limited thereto, but may be modified as appropriate without departing from the gist of the invention.

For example, the embodiment and the modified embodiment are described with reference to a gas sensor element ($NO_x$ sensor element) capable of detecting $NO_x$ concentration. However, the present invention is not limited to a $NO_x$ sensor element, but is applicable to gas sensor elements capable of detecting a gas other than $NO_x$ (e.g., oxygen sensor elements adapted to detect oxygen).

Also, in the modified embodiment, the entirety of the Ip1 positive electrode 212 faces the first porous body 214 such that a portion of the Ip1 positive electrode 212 faces the first porous body 214 with the Ip1 positive lead 216 sandwiched therebetween and such that the remaining portion (a portion free of the lead 216 with respect to the laminating direction) is in contact with the first porous body 214. However, the entirety of the Ip1 positive electrode 212 may be in contact with the first porous body 214 such that the Ip1 positive electrode 212 and the Ip1 positive lead 216 are reversed in position with respect to the laminating direction (vertically reversed in position).

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2013-000999 filed Jan. 8, 2013, Japanese Patent Application No. 2013-035682 filed Feb. 26, 2013, Japanese Patent Application No. 2013-223457 filed Oct. 28, 2013 and Japanese Patent Application No. 2013-231774 filed Nov. 8, 2013, the disclosures of which are incorporated herein by reference in their entirety.

What is claimed is:

1. A gas sensor element configured as a laminate of platelike solid electrolyte bodies, comprising
   electrodes provided on front sides or back sides of the solid electrolyte bodies and
   leads provided on the front sides or the back sides of the solid electrolyte bodies and connected to the electrodes, respectively, wherein
   the electrodes include a water-permeable third electrode disposed within an internal space of the gas sensor element, the internal space communicating with an ambient atmosphere of the gas sensor element;
   the leads include a water-impermeable third lead connected to the third electrode;
   the gas sensor element has a third insulation layer formed on the front side or the back side of the solid electrolyte body;
   the third lead and a portion of the third electrode are formed on the third insulation layer; and
   the third electrode has
   an electrolyte body contact portion which is in contact with the solid electrolyte body through a through hole extending through the third insulation layer in a laminating direction of the solid electrolyte body and
   a third connection portion connected to the third lead on the third insulation layer within the internal space.

2. The gas sensor element as claimed in claim 1, wherein
   the electrodes include a water-permeable fourth electrode which is in contact with a porous body having gas permeability and water permeability and exposed to an ambient atmosphere of the gas sensor element and which is disposed at such a position that the entirety thereof faces the porous body with respect to the laminating direction of the solid electrolyte body;
   the leads include a water-impermeable fourth lead connected to the fourth electrode;
   the gas sensor element has a fourth insulation layer formed on the front side or the back side of the solid electrolyte body;
   the fourth lead and a portion of the fourth electrode are formed on the fourth insulation layer; and
   the fourth electrode has
   an electrolyte body contact portion which is in contact with the solid electrolyte body through a through hole extending through the fourth insulation layer in the laminating direction and
   a fourth connection portion connected to the fourth lead on the fourth insulation layer at such a position as to face the porous body with respect to the laminating direction.

3. The gas sensor element as claimed in claim 1, wherein the gas sensor element detects a concentration of $NO_x$ contained in a gas to be measured, and
   an electric current flows through the first lead or the third lead according to $NO_x$ concentration.

4. A gas sensor comprising the gas sensor element as claimed in claim 1.

* * * * *